United States Patent [19]
Leonard et al.

[11] Patent Number: 5,514,335
[45] Date of Patent: May 7, 1996

[54] BLOOD OXYGENATION SYSTEM AND RESERVOIR AND METHOD OF MANUFACTURE

[75] Inventors: Ronald J. Leonard, Ann Arbor; Erin J. Lindsay, Manchester; David B. Maurer; Daniel W. Viitala, both of Ann Arbor, all of Mich.

[73] Assignee: Minnesota Mining and Manufacturing Company, St. Paul, Minn.

[21] Appl. No.: 142,809

[22] Filed: Oct. 25, 1993

[51] Int. Cl.⁶ .............................. A61M 1/14; A61M 1/34; A61M 1/36
[52] U.S. Cl. .................. 422/46; 422/48; 210/321.6; 210/321.8; 210/321.86; 210/646; 604/4; 604/5
[58] Field of Search .................. 422/46, 48; 210/321.6, 210/321.8, 646, 321.86; 165/96; 604/4, 5, 406

[56] References Cited

U.S. PATENT DOCUMENTS

| | | | |
|---|---|---|---|
| 3,468,631 | 9/1969 | Raible et al. | 23/258.5 |
| 3,615,238 | 10/1971 | Bentley | 23/258.5 |
| 3,757,955 | 9/1973 | Leonard | 210/321 |
| 3,794,468 | 2/1974 | Leonard | 23/258.5 |
| 3,879,293 | 4/1975 | Wolf, Jr. et al. | 210/321 |
| 3,891,416 | 6/1975 | Leonard et al. | 55/178 |
| 3,892,534 | 7/1975 | Leonard | 23/258.5 |
| 3,915,650 | 10/1975 | Talonn et al. | 23/258.5 |
| 3,927,980 | 12/1975 | Leonard | 23/258.5 |
| 3,929,414 | 12/1975 | Leonard | 23/258.5 |
| 3,993,461 | 11/1976 | Leonard et al. | 55/178 |
| 4,026,669 | 5/1977 | Leonard et al. | 23/258.5 |
| 4,061,470 | 12/1977 | Leonard | 23/258.5 |

(List continued on next page.)

FOREIGN PATENT DOCUMENTS

WO90/07943  7/1990  WIPO .
WO93/11808  6/1993  WIPO ............................. A61M 1/36
WO93/25249  12/1993  WIPO ............................. A61M 1/36

OTHER PUBLICATIONS

Brochure entitled "Sarns® SMO/INF Infant Membrane Oxygenator—Instructions"; 3M; Dec., 1989; Form No. 16499401 R/D.
Brochure entitled "Sarns™ SMO/IR Membrane Oxygenator with Integral Reservoir—Instructions"; 3M; Mar., 1990; Form No. 34–9998–9113–7 R/A.
Flyer entitled "SMO/IR Sarns Membrane Oxygenator with Integral Reservoir"; 3M, 1990; Form No. 78–8066–9350–9.
Flyer entitled "SMO/INF Sarns Infant Membrane Oxygenator"; 3M, 1990; Form No. 78–8066–9351–7.
Brochure entitled "When you bring efficiency to the surface . . . you can lower the prime."; 3M; 1990; Form No. 16088004 Rev.B.
Flyer entitled "Sarns Filtered Venous Reservior"; 3M 1991; Form No. 78–8067–3371–9.
Flyer entitled "SMO/ICR Sarns Membrane Oxygenator with Integral Cardiotomy Reservoir"; 3M 1990; Form No. 78–8066–9349–1.

Primary Examiner—Timothy M. McMahon
Assistant Examiner—N. Bhat
Attorney, Agent, or Firm—Gary L. Griswold; Walter N. Kirn; Stephen W. Bauer

[57] ABSTRACT

A novel integral cardiotomy/venous blood reservoir, blood oxygenator and heat exchanging device, method of making a blood oxygenating and heat exchanging device and an extracorporeal circulatory support circuit. The reservoir includes a novel blood defoaming and filtering chamber closely receiving filtering and defoaming media. The blood oxygenating and heat exchanging device includes thermal formed housing portions, and a heat exchanging barrier, blood oxygenating medium and/or filtering medium, which are sealed by potting compound at one time. The oxygenating medium comprises a hollow fiber type medium, with its ends left open to be sealingly mounted in a gas path by a novel mounting bracket.

22 Claims, 35 Drawing Sheets

U.S. PATENT DOCUMENTS

| | | | |
|---|---|---|---|
| 4,149,635 | 4/1979 | Stevens | 206/370 |
| 4,151,088 | 4/1979 | Wolf, Jr. et al. | 210/180 |
| 4,208,193 | 6/1980 | Munsch et al. | 55/36 |
| 4,227,295 | 10/1980 | Bodnar et al. | 29/527 |
| 4,261,951 | 4/1981 | Milev | 422/46 |
| 4,420,085 | 12/1983 | Wilson et al. | 206/571 |
| 4,424,190 | 1/1984 | Mather, III et al. | 422/46 |
| 4,451,562 | 5/1984 | Elgas et al. | 435/2 |
| 4,469,659 | 9/1984 | Carson et al. | 422/46 |
| 4,479,761 | 10/1984 | Bilstad et al. | 417/395 |
| 4,479,762 | 10/1984 | Bilstad et al. | 417/395 |
| 4,559,999 | 12/1985 | Servas et al. | 165/156 |
| 4,568,367 | 2/1986 | Gremel et al. | 55/178 |
| 4,610,656 | 9/1986 | Mortensen | 604/4 |
| 4,643,713 | 2/1987 | Viitala | 604/4 |
| 4,690,758 | 9/1987 | Leonard et al. | 210/247 |
| 4,735,775 | 4/1988 | Leonard et al. | 422/46 |
| 4,759,749 | 7/1988 | Verkaart | 604/113 |
| 4,791,054 | 12/1988 | Hamada et al. | 435/2 |
| 4,818,490 | 4/1989 | Carson et al. | 422/46 |
| 4,846,177 | 7/1989 | Leonard | 128/400 |
| 4,850,954 | 7/1989 | Charvin | 604/4 |
| 4,940,617 | 7/1990 | Baurmeister | 428/36.3 |
| 5,039,430 | 8/1991 | Corey, Jr. | 210/806 |
| 5,039,482 | 8/1991 | Panzani et al. | 422/46 |
| 5,043,140 | 8/1991 | Combs | 422/46 |
| 5,112,480 | 5/1992 | Hukasawa | 210/188 |
| 5,149,318 | 9/1992 | Lindsay | 604/4 |
| 5,152,964 | 10/1992 | Leonard | 422/48 |
| 5,158,533 | 10/1992 | Strauss et al. | 604/4 |
| 5,160,332 | 11/1992 | Nomura | 604/405 |
| 5,192,499 | 3/1993 | Sakai et al. | 422/46 |
| 5,225,161 | 7/1993 | Mathewson et al. | 422/46 |
| 5,236,665 | 8/1993 | Mathewson et al. | 422/46 |
| 5,254,080 | 10/1993 | Lindsay | 604/4 |
| 5,255,734 | 10/1993 | Leonard et al. | 165/96 |
| 5,266,265 | 11/1993 | Raible | 422/46 |
| 5,270,004 | 12/1993 | Cosentino et al. | 422/46 |
| 5,270,005 | 12/1993 | Raible | 422/46 |
| 5,282,783 | 2/1994 | Lindsay | 604/4 |
| 5,382,407 | 1/1995 | Leonard | 422/48 |

BLOOD OXYGENATION SYSTEM AND RESERVOIR AND METHOD OF MANUFACTURE

BACKGROUND OF THE INVENTION

This invention relates generally to extracorporeal blood oxygenation systems, and more particularly to a novel integral venous/cardiotomy blood reservoir, integral blood oxygenation system and method of manufacturing.

SUMMARY OF THE INVENTION

In one aspect of the invention, an integral venous blood and cardiotomy reservoir is provided for use in an extracorporeal circulatory support circuit. Generally, the reservoir comprises a housing having walls defining two interior chambers including a blood storage chamber and a defoaming and filtering chamber. Each chamber has a top and a bottom. The blood storage chamber and defoaming and filtering chamber are separated from one another by a generally vertical dividing wall formed of substantially liquid impervious material. The dividing wall has a vent generally adjacent the top of the defoaming and filtering chamber communicating with the blood storage chamber, and a port generally adjacent the bottom of the defoaming and filtering chamber communicating with the blood storage chamber. At least one cardiotomy blood inlet is provided communicating with the defoaming and filtering chamber for supplying scavenged blood to the reservoir, and at least one venous blood inlet communicating with the defoaming and filtering chamber. A blood filtering medium is provided in the defoaming and filtering chamber for filtering the blood to remove clots and other undesired matter from the blood. The blood filtering medium is positioned in the defoaming and filtering chamber such that blood entering the defoaming and filtering chamber from the cardiotomy blood inlet must pass through the blood filtering medium. A blood defoaming medium is also provided, which takes up substantially the entire space of the defoaming and filtering chamber not occupied by the filtering medium such that blood entering the defoaming and filtering chamber through the cardiotomy blood inlet and venous blood inlet must pass through the blood defoaming medium before exiting the defoaming and filtering chamber through the port.

Preferably, the blood filtering medium is positioned such that blood entering the defoaming and filtering chamber through the venous inlet does not pass through the blood filtering medium. Most preferably, the reservoir includes a generally vertically extending exterior wall forming, together with the dividing wall, the defoaming and filtering chamber, with the cardiotomy blood inlet or inlets being positioned on the exterior wall generally adjacent the top of the defoaming and filtering chamber, and the venous blood inlet or inlets being positioned on the exterior wall generally adjacent the bottom of the defoaming and filtering chamber.

Also, preferably, the walls of the reservoir are formed by thermal forming of thermoplastic material and sealing the walls together along peripheral portions thereof to form the chambers.

An outlet is conveniently provided adjacent the bottom of the blood storage chamber communicating with the interior of the blood storage chamber for draining blood from the blood storage chamber.

In a second aspect of the invention, an integral blood oxygenating and heat exchanging apparatus is provided for oxygenating blood and heating or cooling blood. Generally, the blood oxygenating and heat exchanging apparatus comprises a blood oxygenating and heat exchanging device. The blood oxygenating and heat exchanging device comprises a separation medium (blood oxygenating medium). The separation medium or blood oxygenating medium comprises hollow fibers for separating blood and gas while permitting transfer of oxygen and carbon dioxide across the medium to oxygenate the blood. The separation medium is arranged in an array having opposite ends. A heat exchanging barrier is provided for separating blood and a heat-exchanging fluid while permitting heat transfer across the barrier to heat or cool the blood. The barrier has opposite ends positioned generally adjacent and generally aligned with the opposite ends of the separation medium. A housing holds the separation medium and the heat exchanging barrier. The housing is formed of sheets of thermoplastic material thermal formed into a configuration corresponding to the separation medium and the heat exchanging barrier and having channels for directing potting compound toward the opposite ends of the separation medium and the heat exchanging barrier. Potting compound seals the housing adjacent the ends of the separation medium and heat exchanging barrier. The potting compound is applied by the following process: (a) spinning an assembly of the separation medium, heat exchanging barrier and housing in a centrifuge with the opposite ends of the separation medium and heat exchanging barrier on opposite sides of the axis of rotation of the centrifuge; (b) pouring uncured potting compound into the channels of the housing while the centrifuge is spinning to drive the potting compound toward the opposite ends of the separation medium and heat exchanging barrier; and (c) allowing the potting compound to solidify before stopping rotation of the housing, separation medium and heat exchanging medium in the centrifuge. A blood inlet and outlet are provided into the housing defining a blood flow path across the separation medium and heat exchanging barrier.

Preferably, the separation medium and heat exchanging barriers have opposite surfaces defining the blood flow path and gas or heat-exchanging fluid paths, respectively. The device further comprises a gas inlet and outlet into the apparatus defining a gas flow path along the surface of the separation medium opposite the blood flow path; and a heat exchanging fluid inlet and outlet into the apparatus defining a heat exchanging fluid path along the surface of the heat exchanging barrier opposite the blood flow path.

Also preferably, the housing includes opposite walls along opposite sides of the separation medium, with the blood flow path being defined between the opposite walls of the housing along one surface of the separation medium. The opposite walls are most preferably resiliently-flexible within a range of flexure to allow the opposite walls to be compressed toward one another to adjust oxygenation of blood flowing through the blood flow path.

A mounting bracket is preferably provided for releasably receiving and supporting the device. The mounting bracket is configured to closely receive the device to support the weight of the device and support the housing of the device against internal pressure in the housing. Most preferably, the mounting bracket includes means for compressing the opposite walls of the housing toward one another to adjust oxygenation of blood flowing through the blood flow path. The mounting bracket may also include connections for bringing (a) the gas inlet of the device received in the mounting bracket into fluid communication with a source of gas, and (b) the heat exchanging fluid inlet and outlet of the device received in the mounting bracket into fluid communication with a source of heat exchanging fluid and a conduit for draining heat exchanging fluid, respectively.

A third aspect of the invention is a method of forming an integral blood oxygenating and heat exchanging apparatus. Generally, the method comprises the following steps: (a) providing a separation medium for separating blood and gas from one another while allowing oxygen and carbon dioxide transfer across the separation medium, the separation medium having opposite ends; (b) providing a heat exchanging barrier for separating blood and heat exchanging fluid from one another while allowing heat transfer therebetween across the heat exchanging barrier, the heat exchanging barrier having opposite ends; (c) thermal forming at least one sheet of thermoplastic material to form a housing for receiving the separation medium and heat exchanging barrier with the opposite ends of the separation medium and heat exchanging barrier generally adjacent and generally aligned with one another, the housing forming a channel for directing potting compound adjacent the opposite ends of the separation medium and heat exchanging barrier; (d) placing the separation medium and the heat exchanging barrier between the sheets forming the housing; (e) sealing the sheets together to form an assembly comprising the housing, separation medium and heat exchanging barrier; (f) placing the assembly in a centrifuge; (g) spinning the assembly in the centrifuge with the opposite ends of the separation medium and heat exchanging barrier along opposite sides of the axis of rotation; (h) pouring uncured potting compound into the channel of the housing while the assembly is spinning in the centrifuge; and (i) continue spinning the assembly in the centrifuge until after the potting compound solidifies.

Preferably, a kiln is provided surrounding the centrifuge, and during the steps (g), (h) and (i), the assembly is heated in the kiln while the centrifuge spins the assembly until the potting compound is cured.

In a fourth aspect of the invention, an extracorporeal circulatory support circuit is provided for supporting a patient during cardiopulmonary bypass. Generally, the circuit comprises a blood reservoir having a defoaming and filtering chamber and a blood storage chamber in fluid communication with the defoaming and filtering chamber. The reservoir has at least one cardiotomy blood inlet and at least one venous blood inlet into the defoaming and filtering chamber and an outlet for draining the blood storage chamber. The defoaming and filtering chamber includes defoaming and filtering mediums. A separation medium (blood oxygenating medium) is provided comprising hollow fibers for separating blood and gas while permitting transfer of oxygen and carbon dioxide across the medium to oxygenate the blood. The separation medium is arranged in an array having opposite ends. A heat exchanging barrier is provided for separating blood and a heat-exchanging fluid while permitting heat transfer across the barrier to heat or cool the blood. The barrier has opposite ends positioned generally adjacent and generally aligned with the opposite ends of the separation medium. A housing is provided having portions defining the blood reservoir and holding the separation medium and the heat exchanging barrier. The housing is formed of at least one sheet of thermoplastic material thermal formed into a configuration corresponding to the reservoir, separation medium and heat exchanging barrier. The housing has channels for directing potting compound toward the opposite ends of the separation medium and the heat exchanging barrier. The sheet has portions heat sealed together to form the housing. Potting compound seals the housing adjacent the ends of the separation medium and heat exchanging barrier. The potting compound is applied by the following process: (a) spinning an assembly of the separation medium, heat exchanging barrier and housing in a centrifuge with the opposite ends of the separation medium and heat exchanging barrier on opposite sides of the axis of rotation of the centrifuge; (b) pouring uncured potting compound into the channels of the housing while the centrifuge is spinning to drive the potting compound toward the opposite ends of the separation medium and heat exchanging barrier; and (c) allowing the potting compound to solidify before stopping rotation of the housing, separation medium and heat exchanging medium in the centrifuge. A blood inlet and outlet are provided into the portion of the housing holding the separation medium and heat exchanging barrier. The blood inlet is in fluid communication with the blood outlet of the reservoir. The blood inlet and outlet define a blood flow path across the separation medium and heat exchanging barrier.

Preferably, a blood conduit is provided to bring the outlet of the reservoir into fluid communication with the blood inlet of the portion of the housing holding the separation medium and heat exchanging barrier. The blood conduit is adapted for pumping the blood through the blood conduit from the reservoir into the portion of the housing holding the separation medium and heat exchanging barrier.

Most preferably, a centrifugal blood pump is mounted along the blood conduit to pump blood from the reservoir through the portion of the housing holding the separation medium and heat exchanging barrier. The sheet forming the housing also includes a portion holding the centrifugal blood pump. The centrifugal blood pump may be releaseably held on the sheet.

Alternatively, the blood conduit is formed of resiliently flexible tubing which is adapted to be placed in a positive displacement roller pump to pump blood from the reservoir through the portion of the housing holding the separation medium and heat exchanging barrier.

Also, preferably, the separation medium and heat exchanging barrier have opposite surfaces defining the blood flow path and gas or heat-exchanging fluid paths, respectively. The circuit further comprises a gas inlet and outlet into the portion of the housing holding the separation medium and heat exchanging barrier. The gas inlet and outlet define a gas flow path along the surface of the separation medium opposite the blood flow path. A heat exchanging fluid inlet and outlet are provided into the portion of the housing holding the separation medium and heat exchanging barrier, with the heat exchanging fluid inlet and outlet defining a heat exchanging fluid path along the surface of the heat exchanging barrier opposite the blood flow path.

Most preferably, the housing includes opposite walls along opposite sides of the separation medium, the blood flow path being defined between the opposite walls of the housing along one surface of the separation medium, the opposite walls being resiliently-flexible within a range of flexure to allow the opposite walls to be compressed toward one another to adjust oxygenation of blood flowing through the blood flow path.

Also, preferably, a mounting bracket is provided for releasably receiving and supporting the housing. The mounting bracket is configured to closely receive the portion of the housing holding the separation medium and heat exchanging barrier to support the weight of the housing and its contents and support the housing against internal pressure in the housing. Most preferably, the mounting bracket includes means for compressing the opposite walls of the housing toward one another to adjust oxygenation of blood flowing through the blood flow path.

Preferably, the mounting bracket includes connections for bringing (a) the gas inlet of the housing received in the mounting bracket into fluid communication with a source of gas, and (b) the heat exchanging fluid inlet and outlet of the housing received in the mounting bracket into fluid communication with a source of heat exchanging fluid and a conduit for draining heat exchanging fluid, respectively.

These and other features will be pointed out hereinafter.

BRIEF DESCRIPTION OF THE DRAWING

The invention will be further described with reference to the drawing, wherein corresponding reference characters indicate corresponding parts throughout the several views of the drawing, and wherein.

DETAILED DESCRIPTION OF PREFERRED EMBODIMENTS

Figure 1:
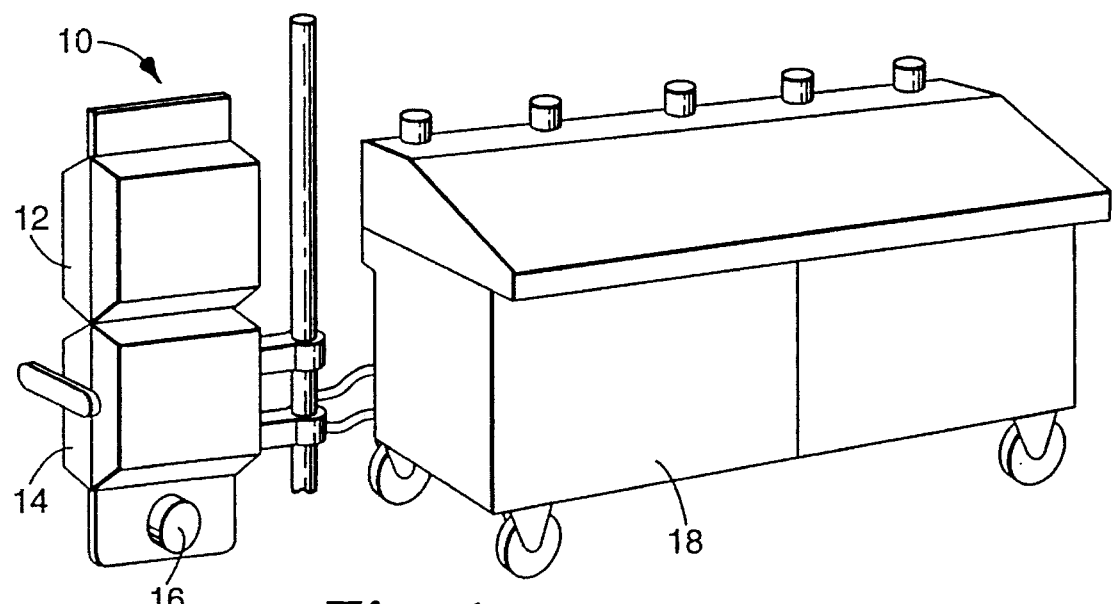
FIG. 1 is a perspective view of a novel integrated circuit, including a blood reservoir, oxygenator, heat exchanger and centrifugal pump, shown mounted in a novel mounting bracket adjacent a perfusion system.

Now referring to the drawing, in particular FIG. 1, the combination of a venous/cardiotomy blood reservoir and an oxygenating and heat exchanging device is designated in its entirety by the reference numeral 10. The combination 10 is adapted to be used to provide extracorporeal support to a patient on cardiopulmonary bypass. The combination 10 is also referred to herein as an integrated circuit (also 10) incorporating pre-connected components, including a novel venous/cardiotomy reservoir 12, a novel blood oxygenating and heat exchanging device 14, and a centrifugal blood pump 16. The circuit 10 is adapted for use with a bank 18 of roller pumps.

Suitable centrifugal pumps 16 are shown in co-assigned U.S. Pat. Nos. 4,589,822; 4,606,698; 4,690,002; 4,778,445; 4,781,525 and 4,984,972 (all of which are hereby incorporated herein by reference), and are available under the trade designation "SARNS™ 7850™ centrifugal pump" from Minnesota Mining and Manufacturing Company, St. Paul, Minn.

The arrangement of the circuit 10 is such that a venous line drains blood from the patient's venous system into the venous/cardiotomy blood reservoir 12, where the blood is defoamed and held, and the bank 18 of roller pumps may be used with cardiac suckers (not shown) to drain blood from the chest wound and deliver the scavenged blood to the cardiotomy portion of the reservoir 12. Blood is then pumped from the outlet of the reservoir 12 by the centrifugal pump 16 into the oxygenating and heat exchanging device 14 for cooling or heating and oxygenating the blood. The blood passes through the outlet of the oxygenating and heat exchanging device 14 into an arterial line which returns the oxygenated blood to the patient's arterial system.

The general route of the blood through the circuit 10 is like that described in co-assigned U.S. Pat. Nos. 5,282,783 and 5,403,273, which are incorporated herein by reference. See, also, PCT Publication No. WO 93/11,808.

The bank 18 of roller pumps may be part of various perfusion systems that are available, for example, under the trade designations "SARNS™ 9000™ Perfusion System"; "SARNS™ MDX™ system"; and "SARNS™ 8000™ Perfusion System" from Minnesota Mining and Manufacturing Company, St. Paul, Minn.

Figure 2:
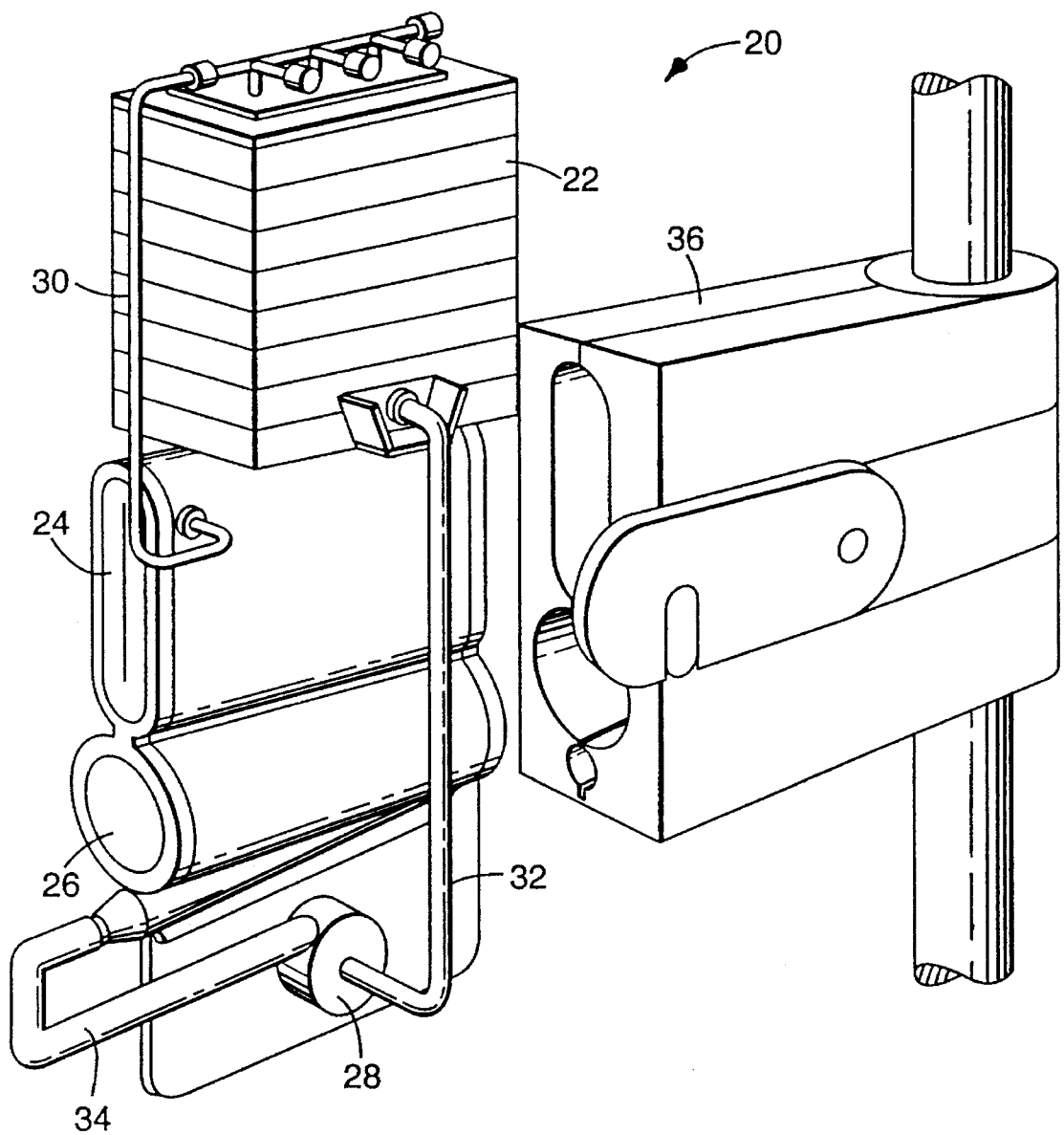
FIG. 2 is a perspective/exploded view of a novel circuit and mounting bracket similar in many respects to that shown in FIG. 1.

FIG. 2 illustrates a second embodiment of the circuit, here designated 20, which includes, starting from the top, a venous/cardiotomy blood reservoir 22, blood oxygenator 24, blood heat exchanger 26 and centrifugal blood pump 28, along with a vent line 30 venting the oxygenator 24 to the top of the reservoir 22.

Although not shown, the oxygenator gas regulating mechanisms described in U.S. Pat. Nos. 5,152,964 and 5,382,407, incorporated herein by reference, may be used in the circuit. In that case, a line (not shown) would be used to provide pressure feedback from the venous line (not shown) to the oxygenator gas regulating mechanism (not shown) to control the gas pressure in the oxygenator.

Line 32 drains the venous/cardiotomy reservoir 22 into the centrifugal blood pump 28. The upstream end of the line 32 is connected with the outlet of the reservoir 22, which is located at or adjacent the bottom of the reservoir 22, and the downstream end of the line 32 is connected with the inlet of the centrifugal blood pump 28, which brings blood into the pump 28 along the axis of rotation of the pump impeller (not shown). Line 34 is connected an outlet along the periphery of the pump 28 and to the heat exchanger 26 to allow blood to be pumped into the heat exchanger 26. The outlet of the centrifugal pump 28 is positioned along the top of the pump 28, and extends along a horizontal tangent of the circumferential peripheral surface of the pump 28.

FIG. 2 also illustrates a reservoir 22 and integral blood oxygenator 24/heat exchanger 26, each of which are made according to a novel process of the invention. The housings of these components are formed, as described below, by thermal forming thermoplastic sheets of material over heated vacuum molds, assembling the components, and providing a potting compound to seal the components while the assembly is spinning in a centrifuge/kiln apparatus illustrated in FIGS. 16–18.

Also shown in FIG. 2 is a novel mounting bracket 36 which is adapted to closely receive the integral blood oxygenator 24/heat exchanger 26 to support the weight and hold the circuit 20 during the use of the circuit 20, and to support the housing of the integral blood oxygenator 24/heat exchanger 26 against internal pressure. It is contemplated that the housing of the integral blood oxygenator 24/heat exchanger 26 would be formed of resiliently flexible material, which while reasonably stiff, allows the walls of the housing to be flexed to vary oxygenator performance. Most preferably, the mounting bracket 36 includes means, such as a manually movable plate, for compressing the opposite walls of the housing of the oxygenator 24 toward one another to adjust oxygenation of blood flowing through the blood flow path of the oxygenator 24.

The mounting bracket 36 preferably includes a mechanism for connecting the heat exchanger 26 with a conduit leading to a suitable source of heat exchanging fluid, such as water, and another conduit for drainage of the heat exchanging fluid. Most preferably, the mechanism is of the type described in co-assigned U.S. Pat. Nos. 4,846,177 and 5,255,734, both of which are incorporated herein by reference. The mechanism described in U.S. Pat. No. 5,255,734 includes a valve that is opened only after the heat exchanger is sealingly held by the mechanism.

The oxygenator fibers or mats preferably have opposite ends which remain open until the oxygenator 24 and heat exchanger 26 are mounted in the mounting bracket 36, with the mounting bracket including mounting hardware and seals to provide a sealed gas path through the oxygenator fibers or mats. The arrangement is preferably such that oxygenator fibers or mats are sealed in one common action with the mechanism described for the heat exchanging fluid. For example, seals (not shown) may be brought into the appropriate sealing relationship with the oxygenator housing at the same time that the seals of the heat exchanging mounting mechanism described above are brought into sealing engagement with the heat exchanger 26.

Alternatively, the heat exchanger may comprise a hollow fiber type heat exchanger, in which the fibers or mat have opposite open ends similar to the oxygenator fibers or mat.

Figure 3:
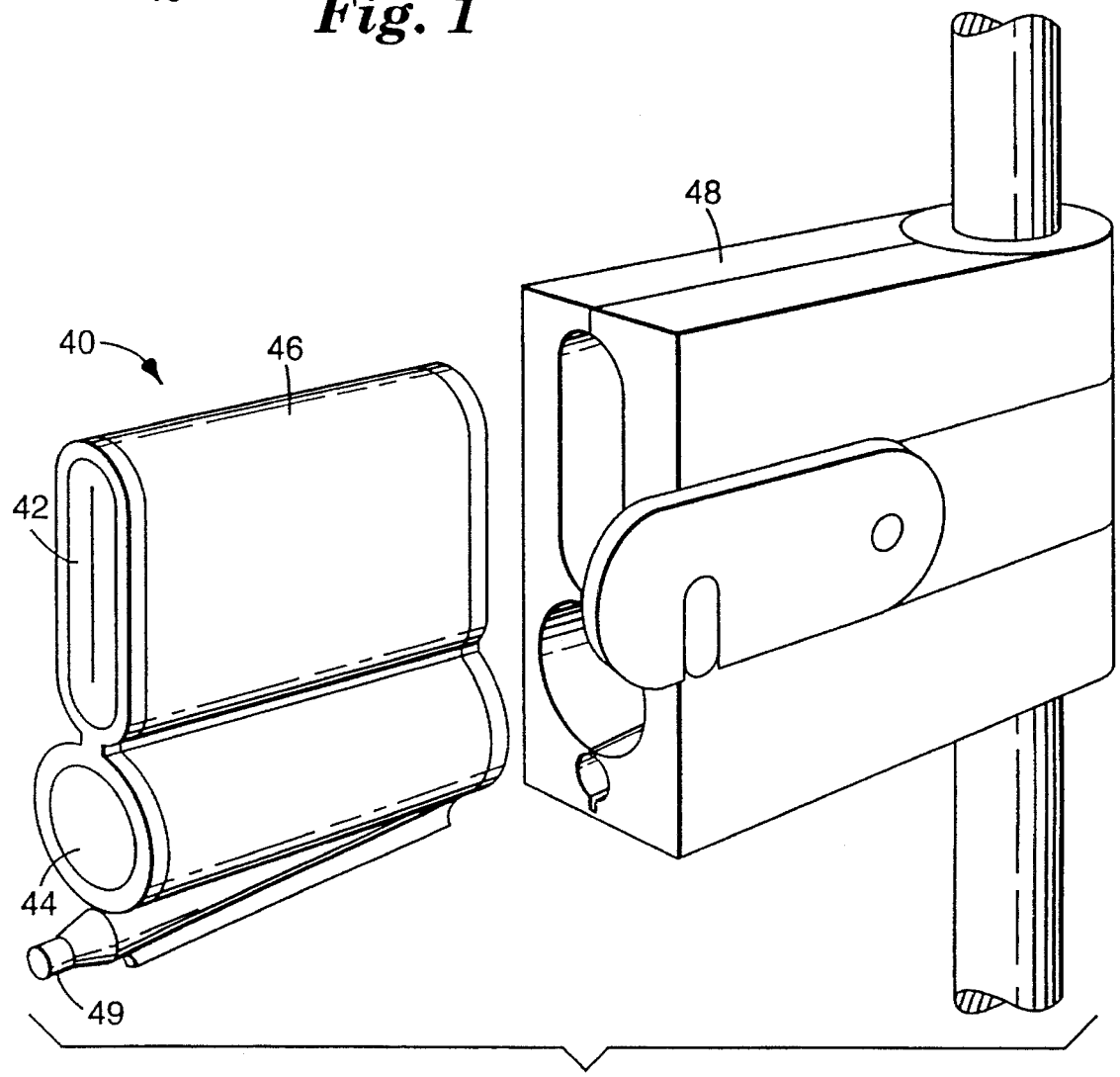
FIG. 3 is a perspective/exploded view of a novel blood oxygenator and heat exchanger apparatus including a novel mounting bracket.

FIG. 3 illustrates a third embodiment of the invention, in which a novel integral oxygenator and heat exchanger, herein designated 40, is provided. The device 40 includes an oxygenator portion 42 and a heat exchanging portion 44 within a housing 46 formed by thermal forming two sheets of thermoplastic material and sealing (preferably heat sealing) the sheets together with rf energy. The device 40 does not include a reservoir, which would be supplied separately. The device 40 is adapted to be closely received in a mounting bracket 48 that is similar to mounting bracket 36 of FIG. 2. The device 40 includes a blood inlet 49 into the heat exchanging portion 44 along the bottom of the heat exchanging portion 44, and a blood outlet (not shown in FIG. 3) from the oxygenating portion 42 along or adjacent the top thereof, thus defining a blood flow path generally upwardly through the device. The device 40 is similar in most respects to the oxygenator 24/heat exchanger 26 of FIG. 2.

Figure 4:
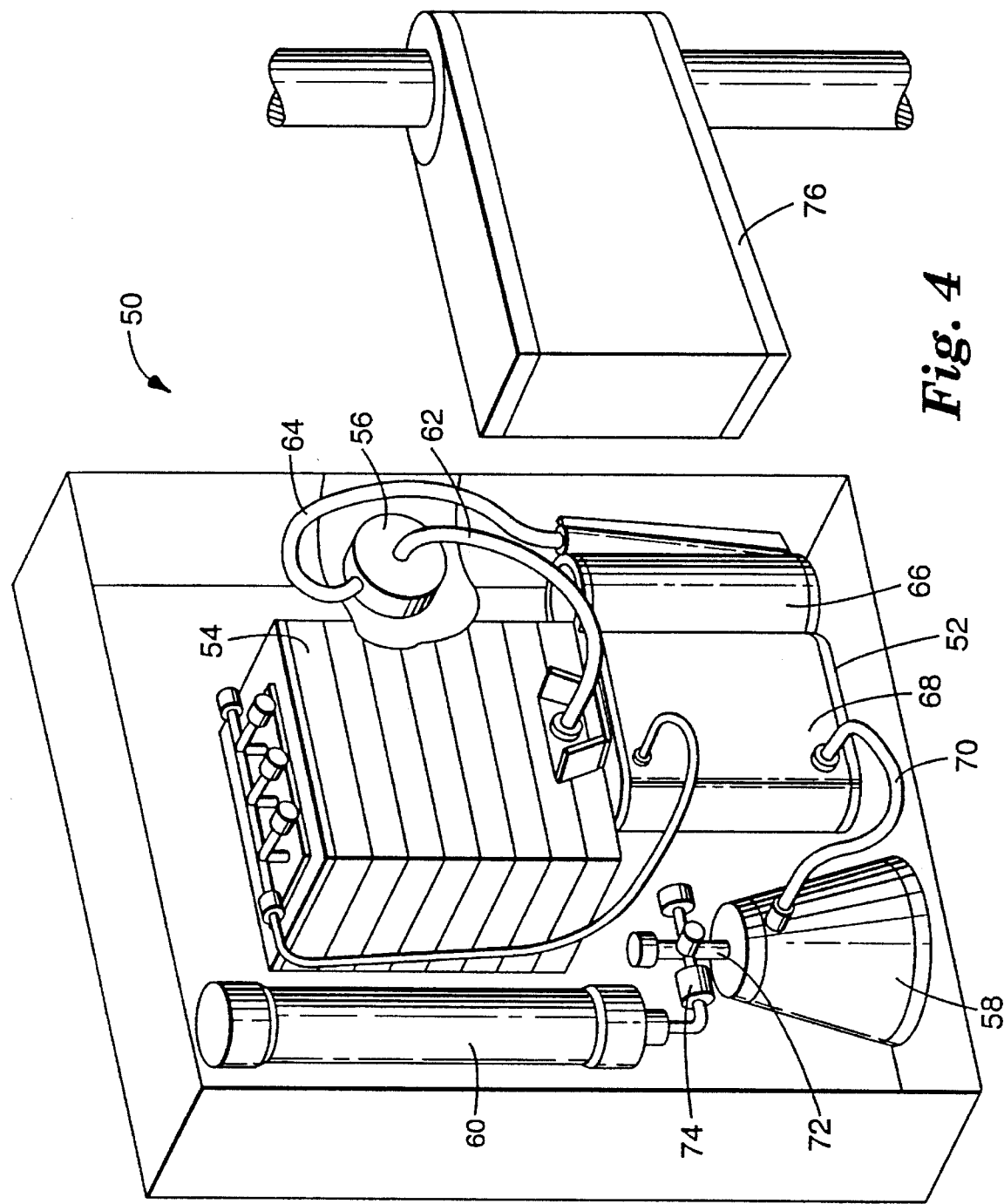
FIG. 4 is a perspective view of another embodiment of a novel integrated circuit, including a blood reservoir, oxygenator, heat exchanger, centrifugal pump and arterial filter.

FIG. 4 shows a fourth embodiment of the circuit, herein designated 50. Circuit 50 is similar in many respects to circuit 20. Circuit 50 may include, in addition to an oxygenating and heat exchanging device 52 similar to device 40 and oxygenator 24/heat exchanger 26 of FIGS. 2 and 3, a reservoir 54, centrifugal blood pump 56, arterial blood filter 58 and hemo-concentrator 60. The oxygenating and heat exchanging device 52 of circuit 50 is turned ninety degrees relative to the oxygenator 24/heat exchanger 26 of circuit 20 so that the oxygenator and heat exchanging portions of the device 52 are arranged in side-by-side relationship. This orientation is believed to facilitate allowing the oxygenating and heat exchanging device 52 to function as bubble collection points.

It is contemplated that the reservoir 54 may take the form of the reservoir 12 or 22 of FIGS. 1 or 2, or the reservoir 100 of FIGS. 5–8. Alternatively, the reservoir 54 may take the form of any off-the-shelf reservoir that is commercially available, such as the one available under the trade designation "SARNS™ Integral Cardiotomy Reservoir" from Minnesota Mining and Manufacturing Company, St. Paul, Minn.

Blood exits the reservoir 54 through an outlet adjacent the bottom of the reservoir 54, and travels upwardly via line 62 to the centrifugal blood pump 56. The outlet of the centrifugal pump 56 extends generally upwardly so that the pump 56 can be gravity primed. The blood is then pumped via line 64 from the centrifugal pump 56 to the heat exchanging portion 66 of the oxygenating and heat exchanging device 52. The heat exchanging portion 66 is along the right side of the device 52 as shown in FIG. 4, with blood flow passing through the heat exchanging portion 66 and then through the oxygenating portion 68 from right to left in the figure, and finally exiting from adjacent the bottom of the left side of the oxygenating portion 68 into a line 70. Line 70 takes the blood to a conventional arterial blood filter 58 of the type commercially available, for example, from Gelman Sciences Inc., Ann Arbor, Mich. The filtered blood travels via line 72 from the arterial blood filter 58 to a valve mechanism 74.

The valve 74 allows the blood to be directed to a conventional hemo-concentrator 60 at the end of surgery to increase the hematocrit and decrease the fluid volume of the blood being reperfused into the patient. As is well known in the art, hematocrit is the percentage volume of blood occupied by cells. During cardiopulmonary bypass, the blood is diluted with saline solution to increase blood volume without or with minimum donated blood. For example, the extracorporeal support circuit may be primed with saline solution before the patient is supported by that circuit, with the saline prime diluting the patient's blood. Accordingly, a hemo-concentrator 60 may be provided to increase the hematocrit of the otherwise diluted blood. The valve 74 also allows blood to be reperfused directly to the patient during surgery, bypassing the hemo-concentrator 60.

FIG. 4 also shows a mounting bracket 76 similar in many respects to mounting brackets 36 and 48 of FIGS. 2 and 3. The orientation of the supporting surfaces of mounting bracket 76, which support the oxygenating and heat exchanging device 52 is different to accommodate the different orientation of the oxygenating and heat exchanging device 52.

FIGS. 5–8 illustrate a novel integral venous/cardiotomy blood reservoir 100 of the invention. The reservoir 100 comprises a housing 102 having walls defining two interior chambers 104 and 106 including a blood storage chamber 104 and a defoaming and filtering chamber 106. Each chamber 104 or 106 has a top and a bottom. The blood storage chamber 104 and defoaming and filtering chamber 106 are separated from one another by a generally vertical dividing wall 108 formed of substantially liquid impervious material. The dividing wall 108 has a vent 110 generally adjacent the top of the defoaming and filtering chamber 106 communicating with the blood storage chamber 104, and a port 112 generally adjacent the bottom of the defoaming and filtering chamber 106 communicating with the blood storage chamber 104. The defoaming and filtering chamber 106 is the interior space defined by the dividing wall 108, a generally vertically extending exterior wall 114 and the side and top and bottom walls extending between the exterior wall 114 and the dividing wall 108.

At least one, preferably four, cardiotomy blood inlets 116 communicate with the defoaming and filtering chamber 106 for supplying scavenged blood to the reservoir 100, and at least one venous blood inlet 118 communicates with the defoaming and filtering chamber 106. Preferably, the cardiotomy blood inlets 116 are positioned on the exterior wall 114 generally adjacent the top of the defoaming and filtering chamber 106, and the venous blood inlet 118 is positioned on the exterior wall 114 generally adjacent the bottom of the defoaming and filtering chamber 106. A blood outlet 120 is provided at/adjacent the bottom of the blood storage chamber 104 to allow drainage to blood stored in the blood storage chamber 104 to a blood pump, such as any suitable conventional positive-displacement roller pump or centrifugal blood pump.

A blood filtering medium 122 is provided in the defoaming and filtering chamber 106 for filtering the blood to remove clots and other undesired matter from the blood. The blood filtering medium 122 is positioned in the defoaming and filtering chamber 106 such that blood entering the defoaming and filtering chamber 106 from the cardiotomy blood inlets 116 must pass through the blood filtering medium 122, but such that blood entering the defoaming and filtering chamber 106 through the venous inlet 118 does not pass through the blood filtering medium 122. The blood filtering medium 122 may comprise, for example, a pleated composite structure of two layers of extruded polyethylene with a layer of polyester filter material sandwiched between the polyethylene layers, such as available for several manufacturers including Tetko Inc., Briarcliff, N.Y. The periphery of the blood filtering medium 122 is sealed to the reservoir walls to ensure that blood entering through the cardiotomy inlets 116 passes through the filtering medium 122.

A blood defoaming medium 124 is also provided, with the blood defoaming medium 124 taking up substantially the entire space of the defoaming and filtering chamber 106 not occupied by the filtering medium 122 such that blood entering the defoaming and filtering chamber 106 through the cardiotomy blood inlets 116 and venous blood inlet 118 must pass through the blood defoaming medium 124 before exiting the defoaming and filtering chamber 106 through the port 112.

The blood defoaming medium 124 may comprise, for example, a conventional open cell polyurethane foam having approximately 20 pores per inch, with high molecular weight silicone solution added to the foam as is conventional. Most preferably three layers of such foam material are used, with one section 124A of such foam being placed between the filtering medium 122 and the cardiotomy inlets 116.

The feature of the blood defoaming medium 124 and filtering medium 122 taking up substantially the entire space between the walls forming the defoaming and filtering chamber 106 is believed to improve the defoaming action of the reservoir 100.

Figure 8:
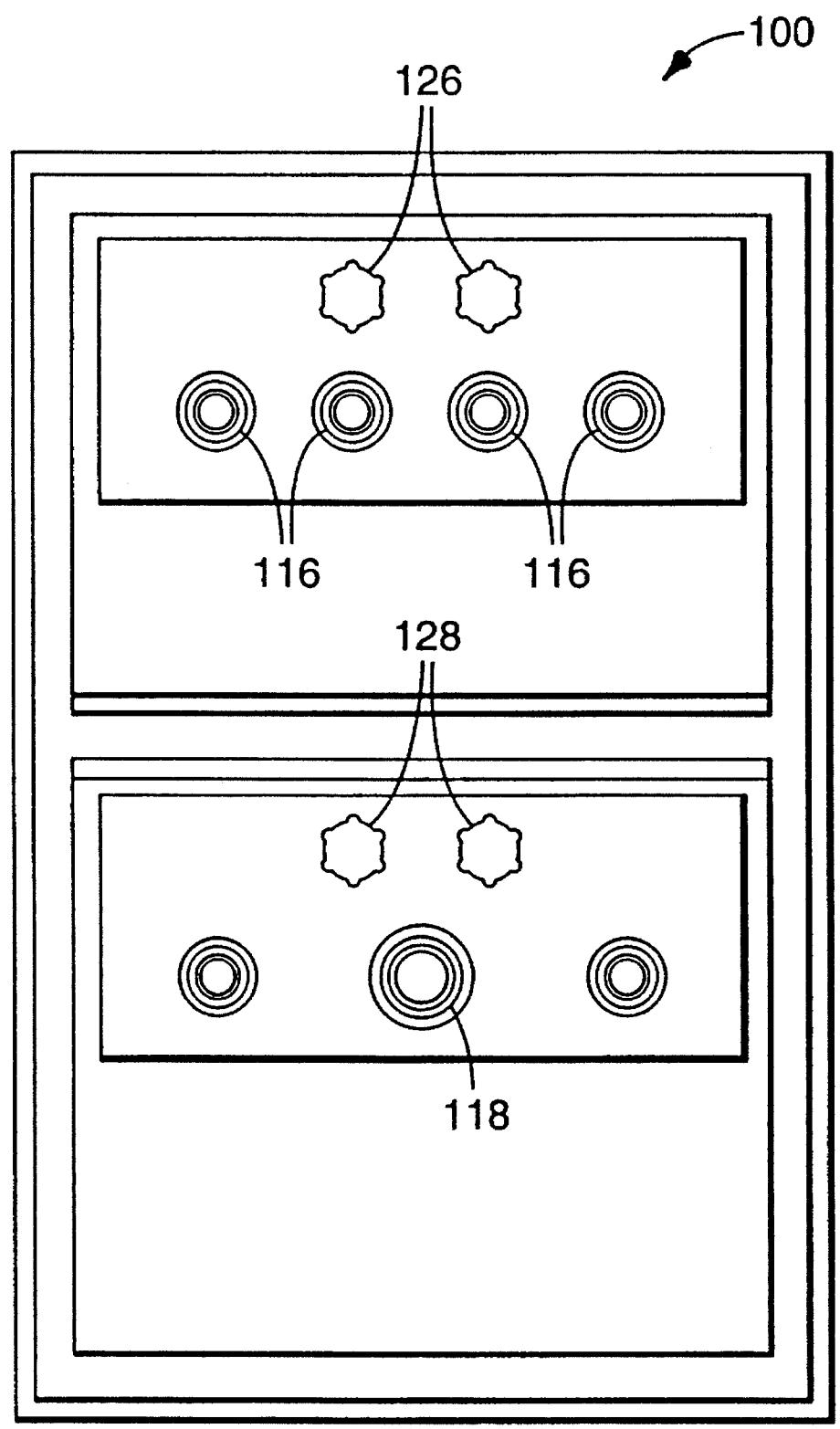
FIG. 8 is a back view of the reservoir of FIGS. 5–7, showing various connections, including cardiotomy inlet connections and venous blood inlets.

As best illustrated in FIG. 8, conventional luer type connection ports 126 and 128 are provided generally adjacent the cardiotomy inlets 116 and venous inlet 118.

Figure 5:
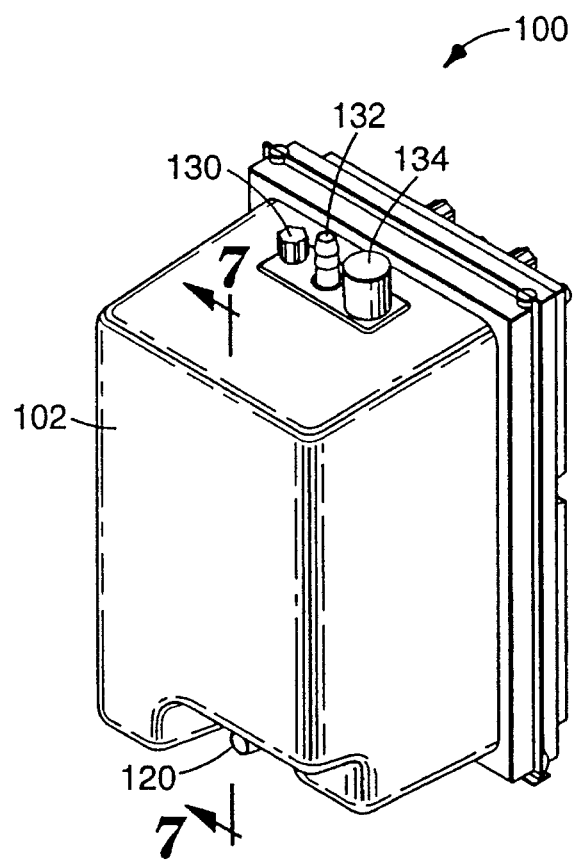
FIG. 5 is a perspective view of a novel integral venous blood and cardiotomy reservoir of the invention.
Figure 6:
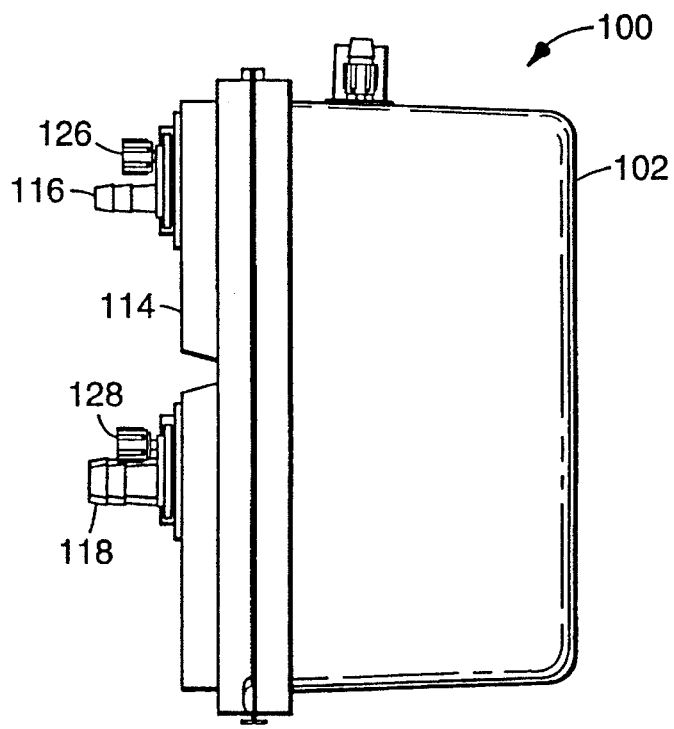
FIG. 6 is a left side view of the reservoir of FIG. 5.
Figure 7:
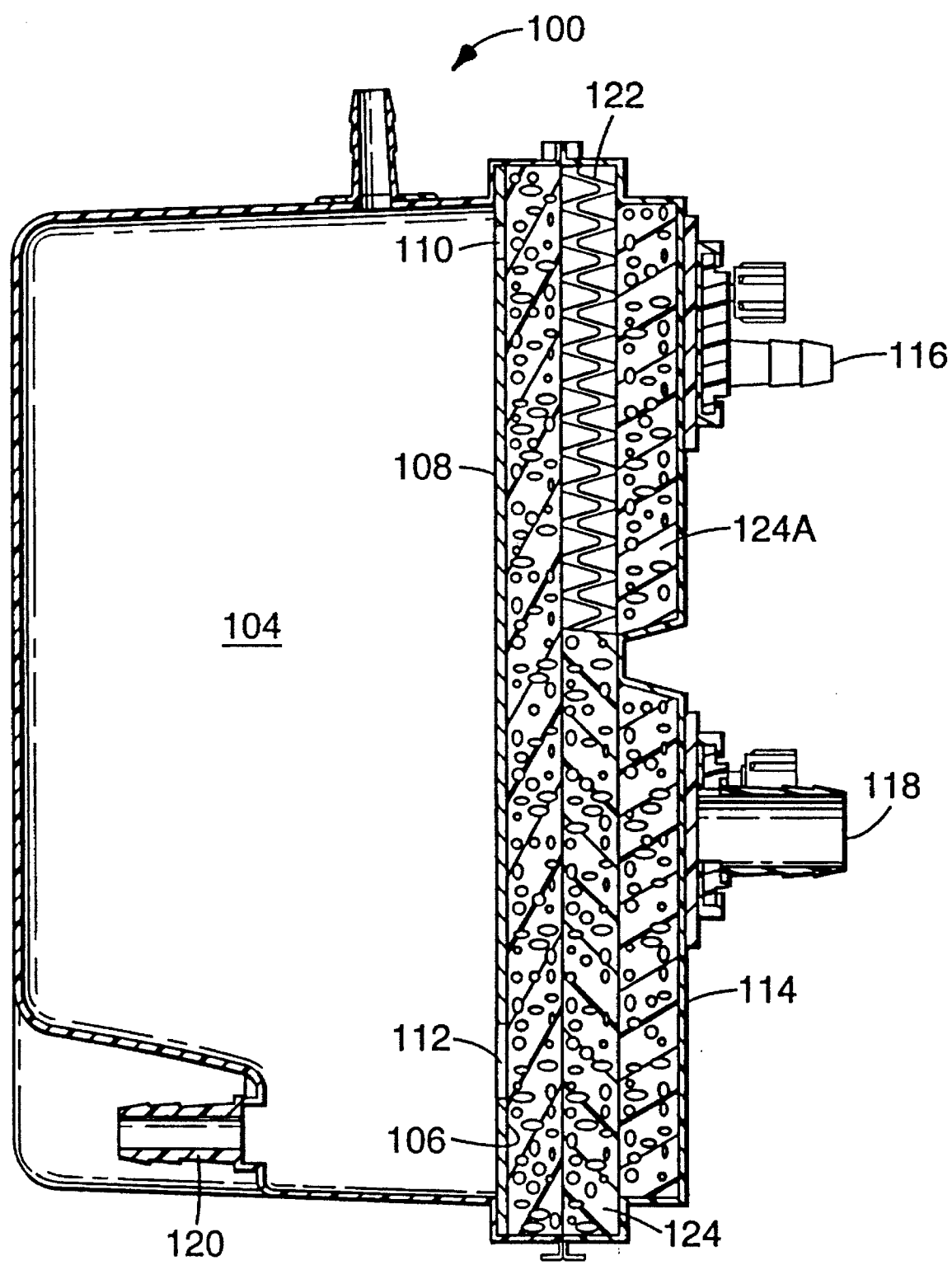
FIG. 7 is a generally vertical cross sectional view substantially along line 7—7 of FIG. 6, showing a novel defoaming and filtering chamber of the reservoir of FIGS. 5 and 6.

Also provided in FIG. 5 are a luer type port 130 for a vacuum line (not shown), a tube connection post 132 for an overflow line (not shown) and a pressure/vacuum control valve 134. These features facilitate use of the reservoir 100 as a post surgical chest drainage container.

Most preferably, the walls of the reservoir 100 are formed by thermal forming of thermoplastic material and sealing the walls together along peripheral portions thereof to form the chambers 104 and 106. Most preferably, the thermoplastic material is polyethylenetetrathalate ("PETE") sheets having a thickness of approximately 0.030–0.060 inches (0.76–1.52 mm).

The reservoir 100 may be formed with volume markings (not shown) including a marking designating the minimum desired operating level.

Figure 9:
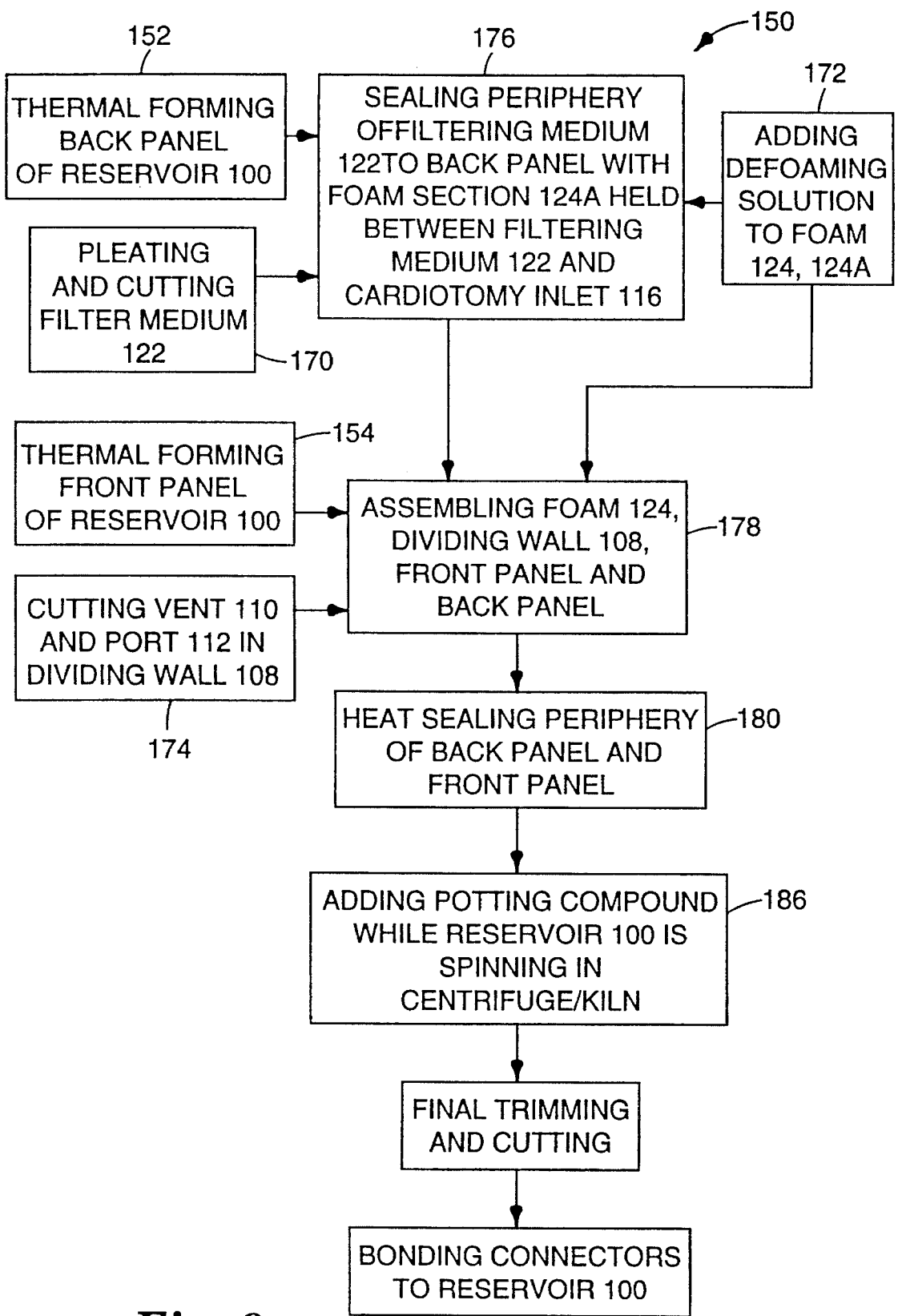
FIG. 9 is a flow chart illustrating the process of making the reservoir of FIGS. 5–8.

FIG. 9 is a flow chart illustrating the manufacturing process 150 for making the reservoir 100. The process includes steps 150 and 152 of thermal forming the sheets of thermoplastic (preferably PETE) material on the aluminum molds 154 and 156 shown in FIGS. 10A and 10B to form the back and front panels of the reservoir 100. Initial cutting of the sheets may be done during the thermal forming steps. For example, openings for inlets and outlets may be cut while the formed sheets are on the thermal forming molds 154 and 156.

Figure 10A:
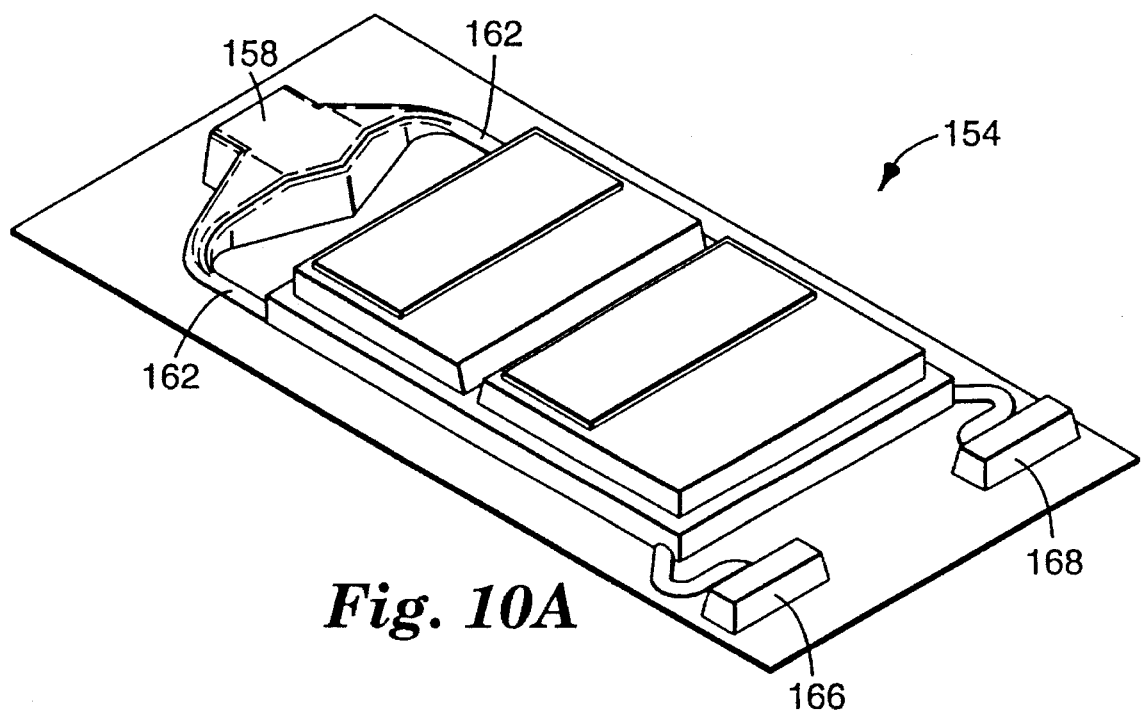
FIGS. 10A and 10B are perspective views of vacuum molds useful for thermal forming sheets of thermoplastic material into the desired configuration for the reservoir of FIGS. 5–8.
Figure 10B:
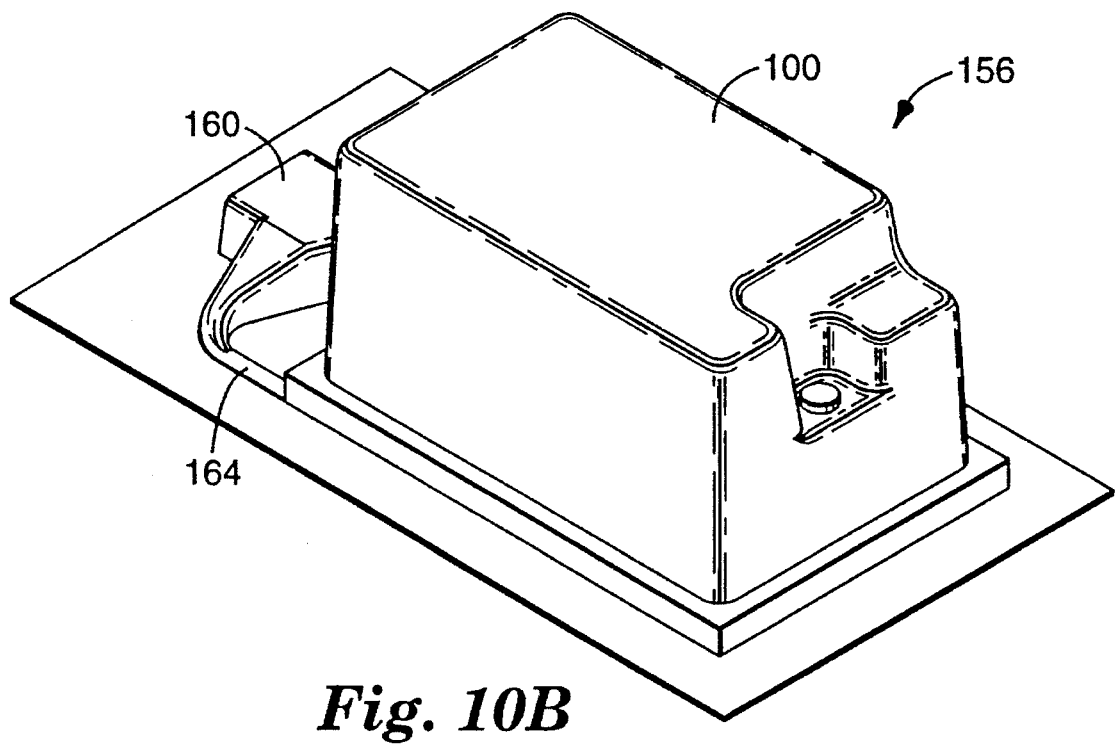

As best illustrated in FIG. 10A, the molds are designed to form sheets having various features relating to further processing of the reservoir 100. These include forming a potting "boat" on the boat-forming features 158 and 160 of the molds 154 and 156 adjacent the top of the back and front sheets, with the resulting potting boat (not shown) facilitating adding and distributing potting compound in a further processing step. The resulting potting boat will have a generally wide, V-shaped bottom corresponding to the bottom of the boat-forming features 158 and 160, with the bottom sloping gently upward from its center to opposite potting channels formed on channel-forming features 162 and 164 along opposite sides of the molds 154 and 156. This sloped V-shaped bottom of the boat facilitates even distribution of the potting compound to the potting channels when potting compound is later added.

Another feature is the overflow reservoirs (not shown) formed on the overflow-forming features 166 and 168 of the molds 154 and 156. The resulting overflow reservoirs include inlets for potting compound that are positioned inwardly from the sides of the reservoir to gauge the depth of potting compound along each side of the reservoir 100 so that potting compound does not reach the overflow reservoirs until the depth of compound reaches the inlets.

Referring again to the flow chart of FIG. 9, the process 150 also includes the initial step 170 of pleating and cutting material to form the blood filtering medium 122. Such pleating may be done in a continuous fashion on roll stock on what is known as a conventional "Grabowski" pleater. Initial step 172 refers to adding conventional defoaming solution to the foam layers and sections 124 and 124A. Initial step 174 is cutting a sheet of thermoplastic material (preferably PETE) to form the dividing wall 108 with a vent 110 and port 112.

Step 176 is to place the section 124A of foam into the cardiotomy portion of the back panel, and seal the periphery of the pleated and cut blood filtering medium 122 to the back panel so as to hold the foam section 124 between the filtering medium 122 and the cardiotomy inlets 116. This partially assembled subassembly is then assembled in step 178 with the other sections of foam 124, the dividing wall 108 and the front panel.

Figure 11:
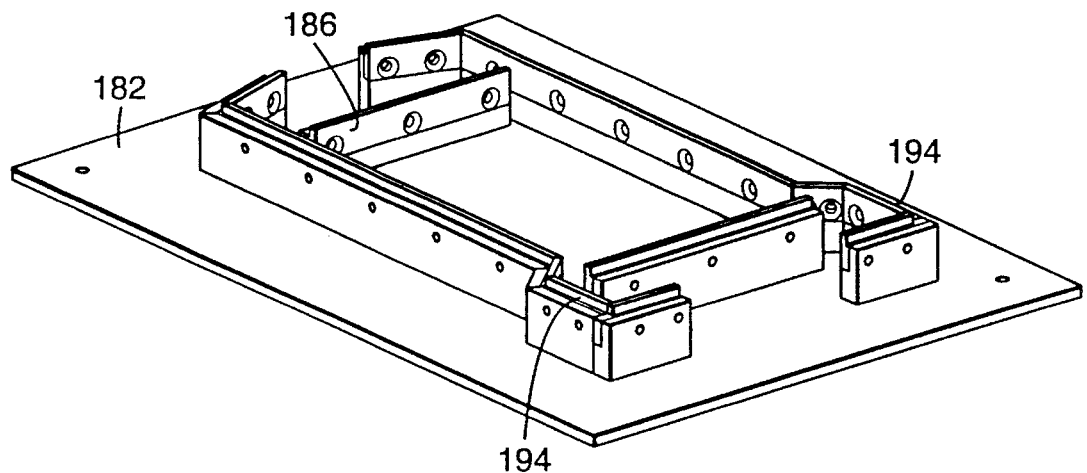
FIGS. 11 and 12 are perspective views of radiofrequency-driven heat sealing apparatus for sealing the sheets formed by the vacuum molds of FIGS. 9 and 10 together to form the reservoir of FIGS. 5–8.
Figure 12:
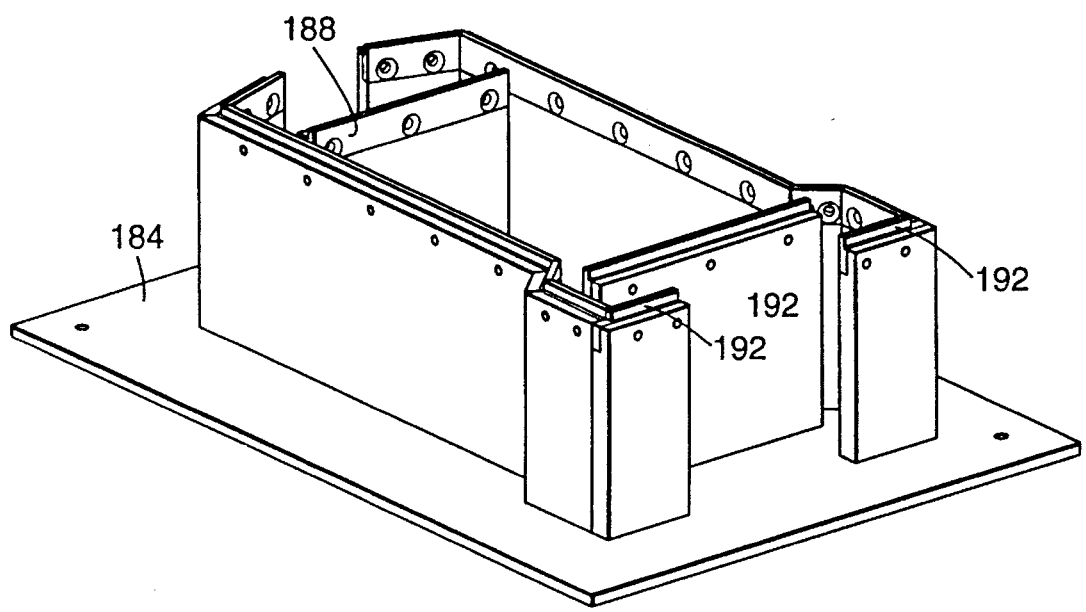

Step 180 is heat sealing along the periphery of the front and back panels and dividing walls together to form the reservoir 100, as well as heat sealing some additional features. FIGS. 11 and 12 show two halves 182 and 184 of an "rf" heat sealing fixture which may be used in step 180. The "rf" heating fixture 182 and 184 includes various rf heat sealing bars arranged in such a manner as to seal the front and back panels with the dividing wall 108 between them, while also sealing the panels so as to further form the potting boat, potting channels and potting overflow reservoirs. For example, rf heat sealing bars 186 and 188 are positioned to form a heat seal between the potting boat and the top of the reservoir 100A (FIG. 13), and three rf heat sealing bars (at 190 and 192) are arranged to form a heat seal around the overflow inlets and overflow reservoirs. Reservoir 100A refers to the assembled reservoir components, with the front and back panels and dividing wall heat sealed together.

Figure 13:
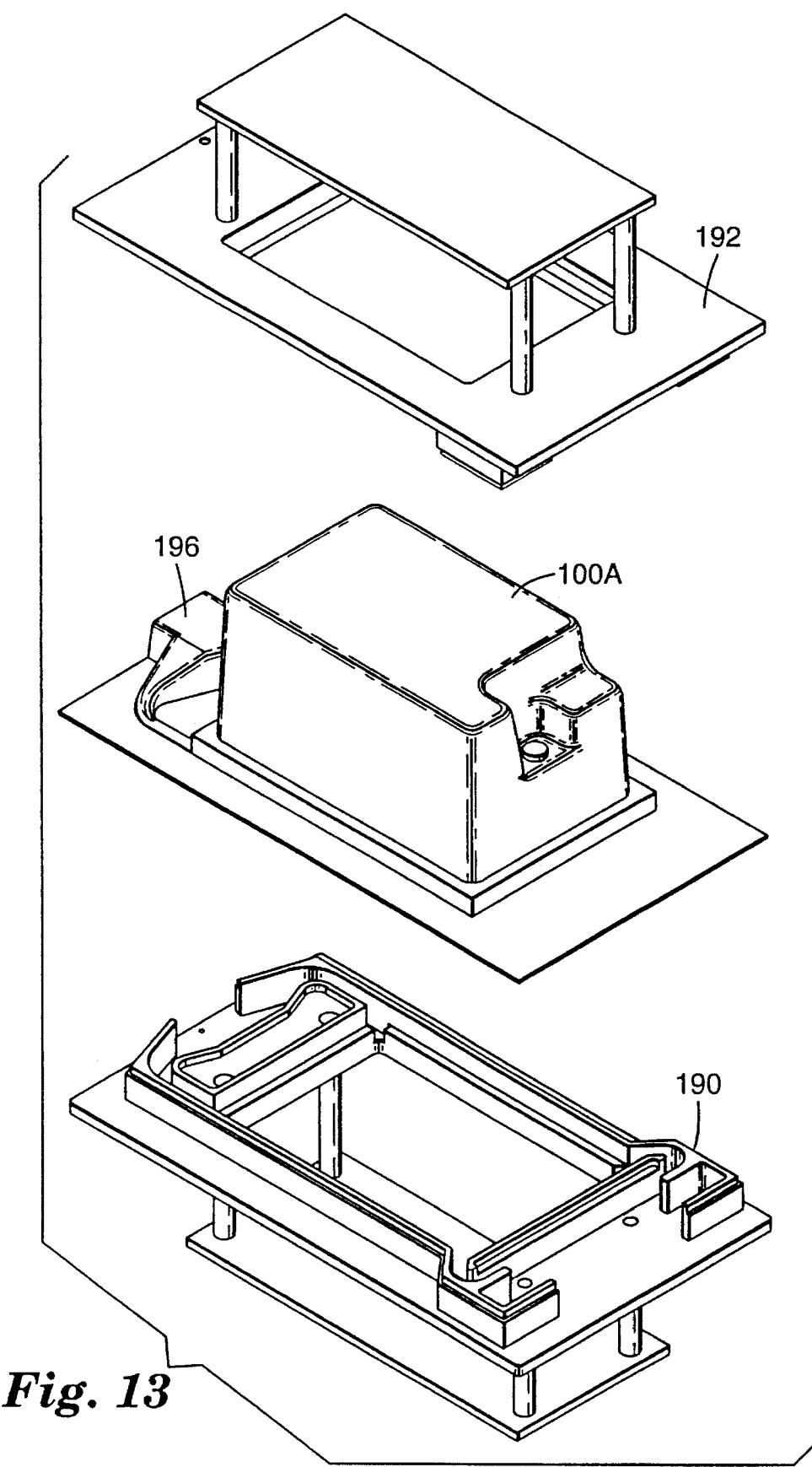
FIG. 13 is an exploded perspective view of the heat sealing apparatus of FIGS. 11 and 12 showing formed but unsealed housing sheets.
Figure 14:
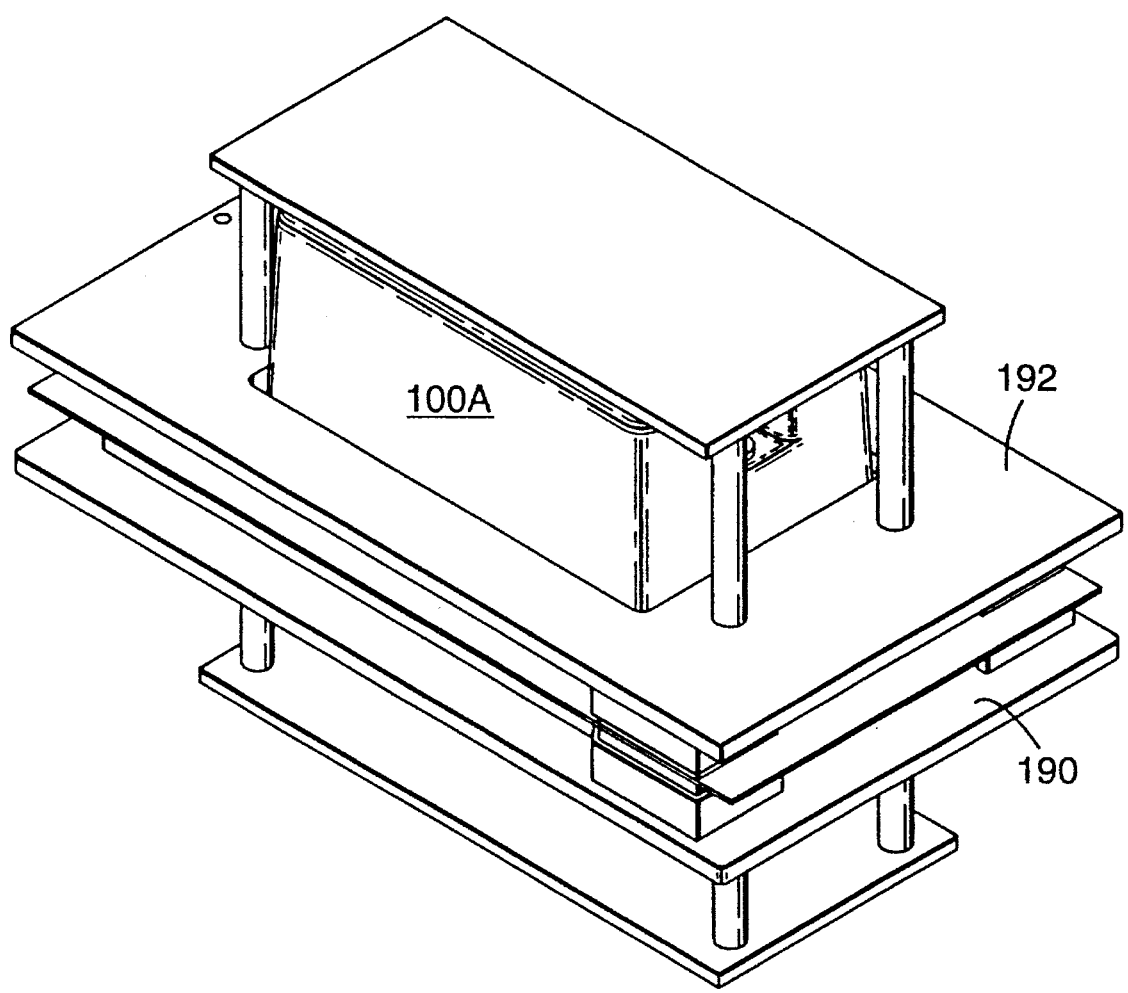
FIG. 14 is a perspective view of the heat sealing apparatus of FIGS. 11–13 with the heat sealing dies holding formed but unsealed housing sheets.
Figure 15:
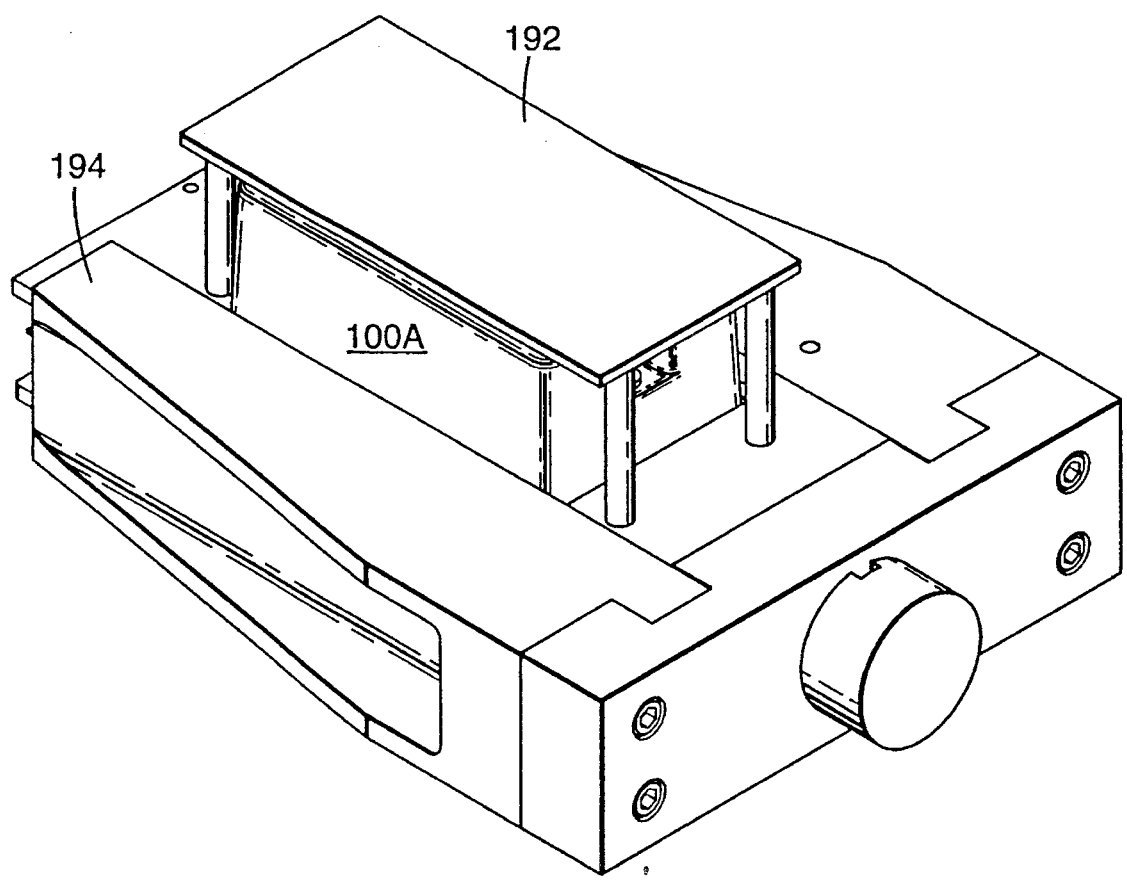
FIG. 15 is a perspective view of the apparatus of FIG. 14 in a clamp for holding the die halves of the heat sealing apparatus together.
Figure 16:
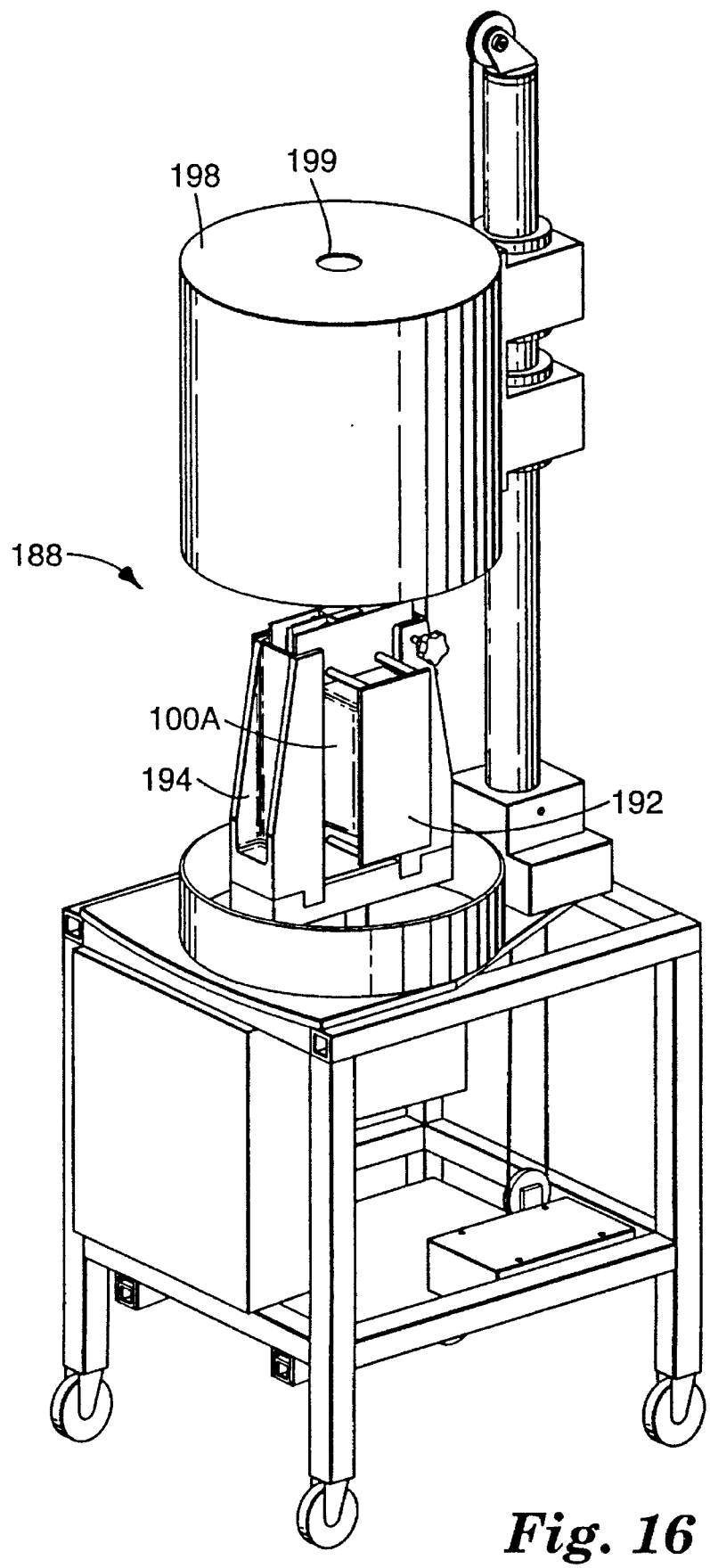
FIG. 16 is a perspective view of a kiln/centrifuge apparatus used in potting the reservoir and/or oxygenating/heat exchanging apparatus of the invention, shown with the clamp and heat sealing apparatus of FIGS. 11–15.
Figure 17:
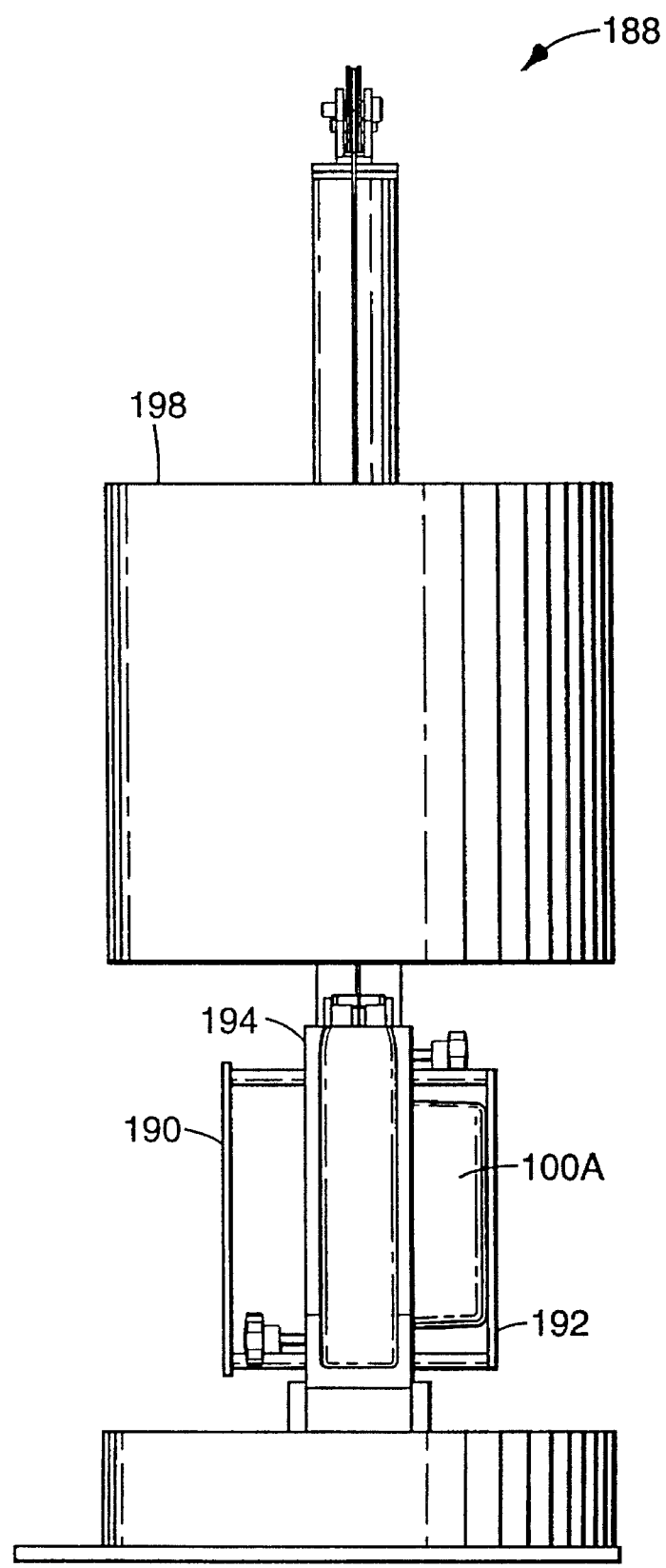
FIG. 17 is a frontal elevation of the kiln/centrifuge apparatus of FIG. 16.
Figure 18:
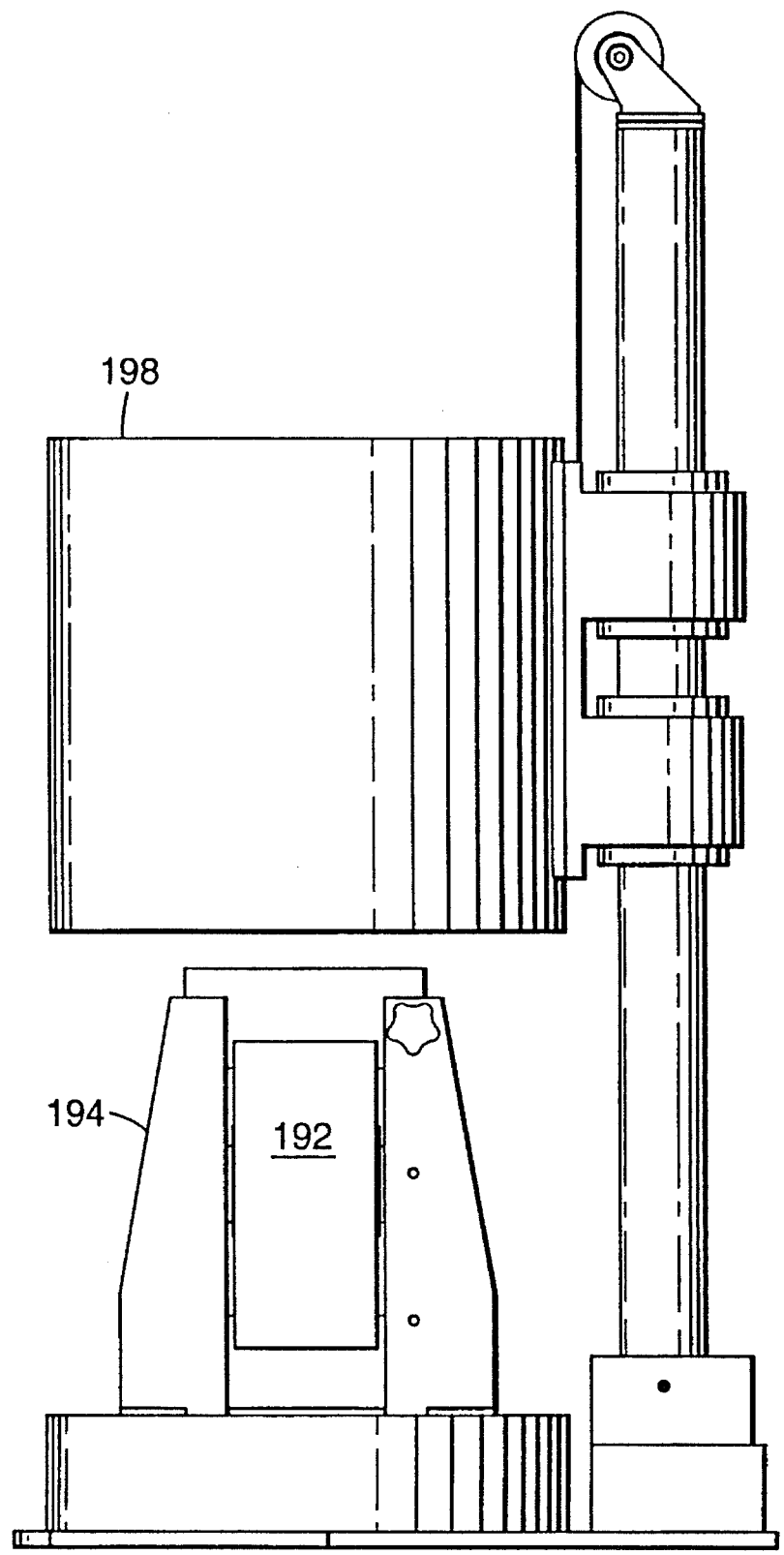
FIG. 18 is a side elevational view of the kiln/centrifuge apparatus of FIGS. 16 and 17.
Figure 19:
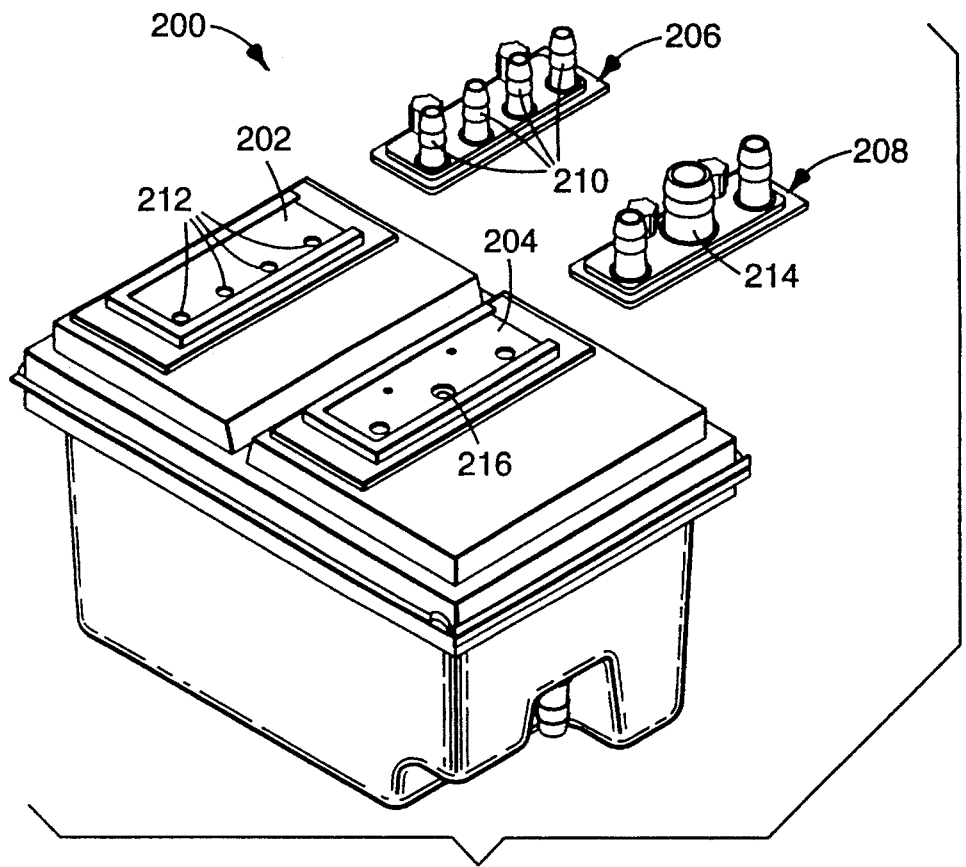
FIGS. 19–21 are rear perspective views of an alternative embodiment of the reservoir of FIGS. 5–8, illustrating a reservoir having a quick-changeover connection assembly for converting the reservoir to different uses.
Figure 20:
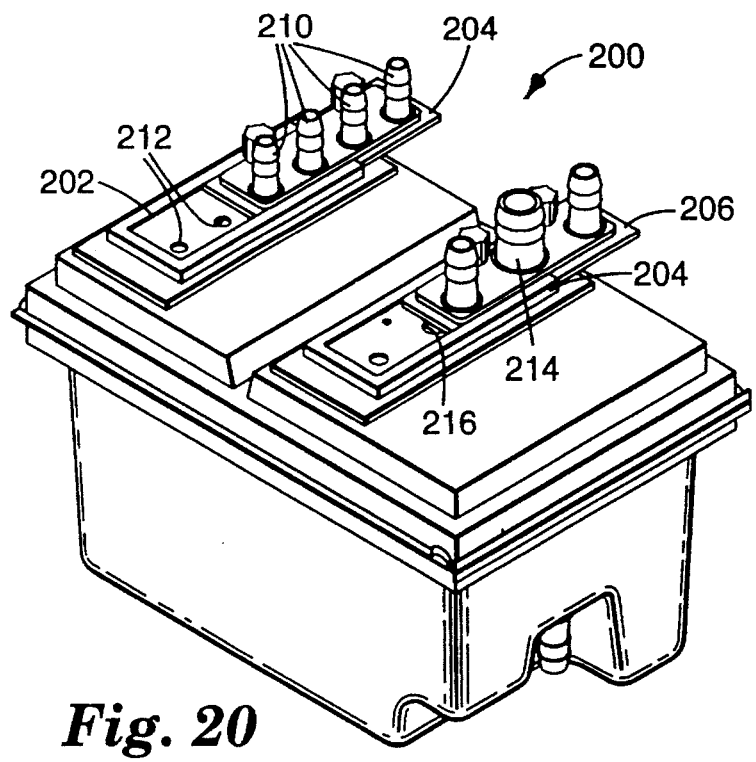

Step 186 is to place the heat sealed assembly into a centrifuge/kiln 188 shown in FIGS. 16–18, and add potting compound (preferably urethane resin) while spinning the assembled reservoir 100A. FIGS. 13 and 14 illustrate preferred pressure plates 190 and 192 which hold the assembled, sealed reservoir 100A in the jaws of a vice 194 shown in FIGS. 15–18, with the potting boat 196 (FIG. 13) facing upwardly and the overflow reservoirs (not shown) generally adjacent the bottom. The centrifuge/kiln 188 includes a hood 198 which contains the vice 194 and assembled reservoir 100A for heating and spinning the reservoir 100A. An opening 199 is provided in the hood 198 to allow potting compound to be added to the reservoir 100A while the reservoir 100A is spinning at a controlled, high temperature (preferably about 150° F. (65° C.)).

FIGS. 19–25 illustrate various aspects of another preferred embodiment of the reservoir, here designated 200. Reservoir 200 includes many features similar in some respects to those shown in U.S. Pat. Nos. 5,149,318; 5,254,080 and 5,399,156, all of which are incorporated herein by reference. Reservoir 200 is similar in most respects to reservoir 100, particularly with respect to the internal structure of the reservoirs.

Figure 21:
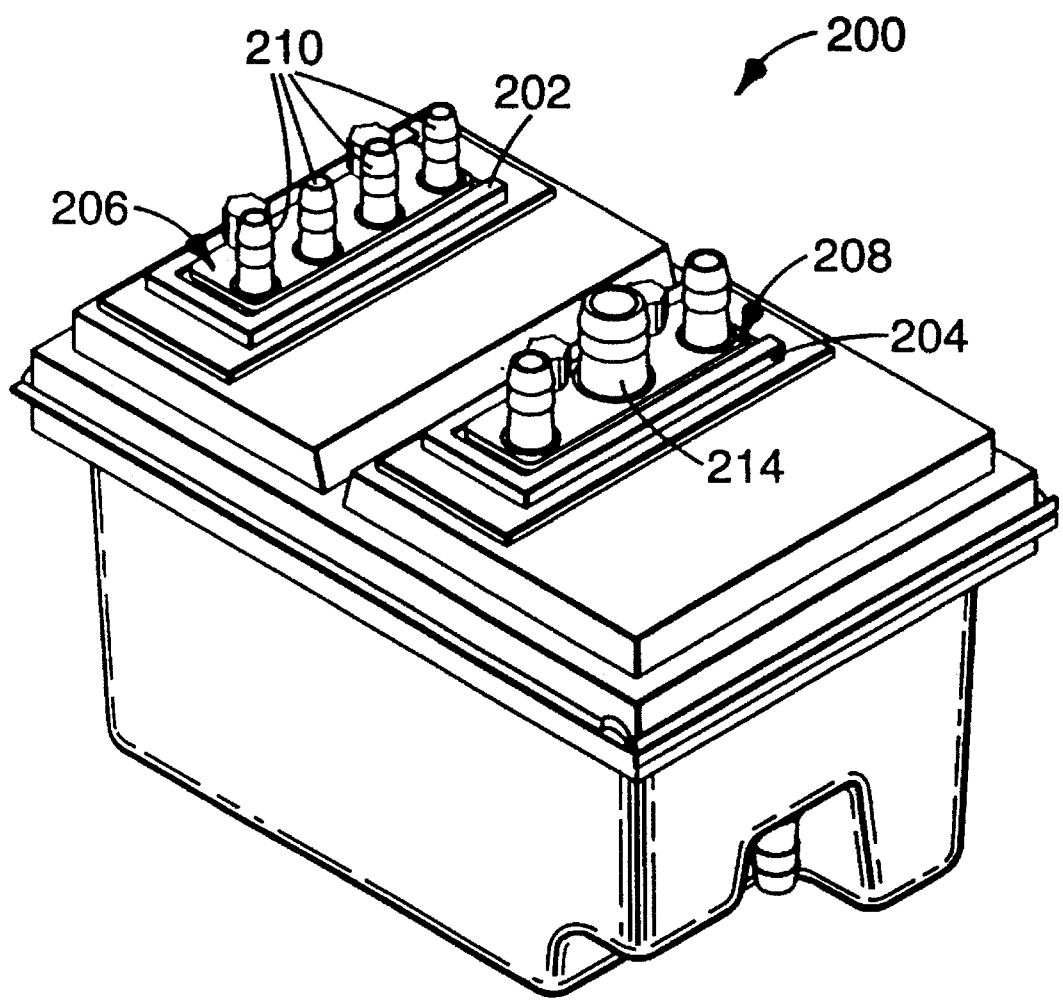

Unlike reservoir 100, however, reservoir 200 has two tracks or track means 202 and 204 each for slidably receiving its respective connector or other block 206 or 208. The arrangement is such as to facilitate conversion of the reservoir 200 from its use as a venous/cardiotomy reservoir, to a use after surgery collecting blood drained from the chest cavity. FIGS. 19–22 show features relating to use of the reservoir 200 during surgery. Connector block 206 may be referred to as a cardiotomy connector block 206, and it includes a plurality, preferably four, cardiotomy inlets connection posts 210 that are brought into sealed fluid communication with inlet bores 212 (FIG. 19) when the cardiotomy connector block 206 is fully inserted into track 202 (FIG. 21). Connector block 208 may be referred to as a venous connector block 208, and it includes at least one venous inlet connection post 214 that is brought into sealed fluid communication with the inlet bore 216 (FIG. 19) when the venous connector block 208 is fully inserted into track 204 (FIG. 21).

Figure 22:
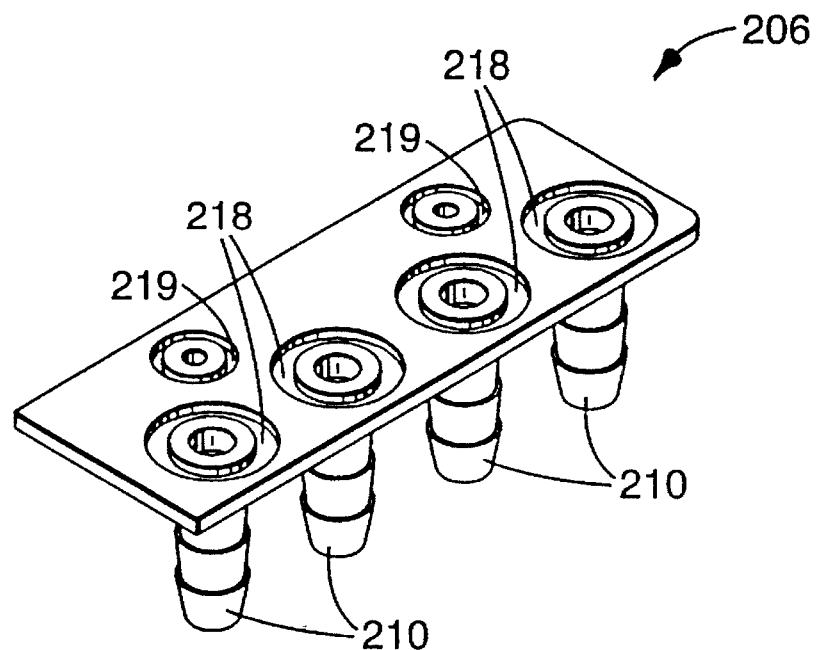
FIG. 22 is a perspective view of a "cardiotomy" connecting block adapted to be slidably received in the upper tracks on the reservoir of FIGS. 13–15 to provide connections for supplying scavenged blood to the cardiotomy section of the reservoir.
Figure 23:
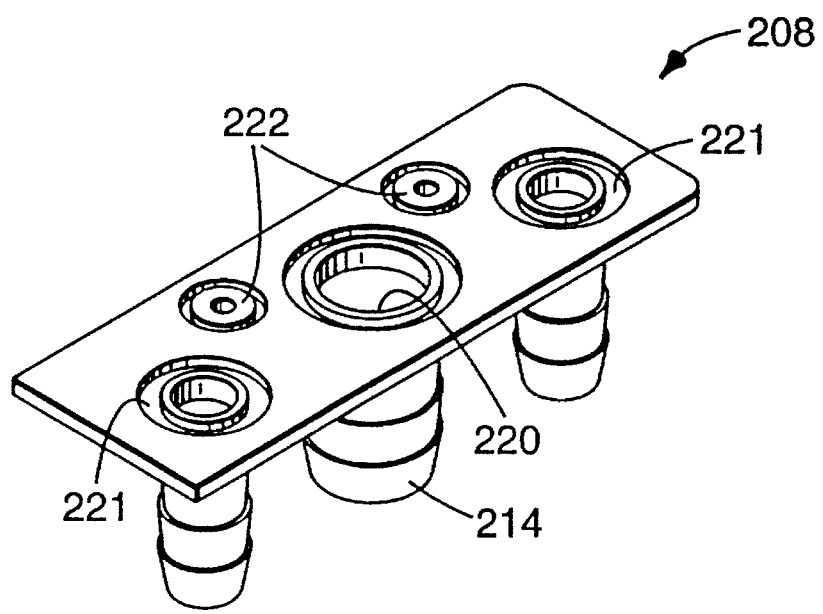
FIG. 23 is a perspective view of a "venous" connecting block adapted to be slidably received in the lower tracks on the reservoir of FIGS. 19–21 to provide connections for supplying venous blood to the defoaming section of the reservoir.

Further details of the connector blocks 206 and 208 are shown in FIGS. 22 and 23, including O-ring seal receiving channels 218, 219, 220, 221 and 222 which receive O-ring seals (not shown) to seal around the interface between the connector blocks 206 and 208 and the base defined between the rails of the tracks 202 and 204.

Figure 24:
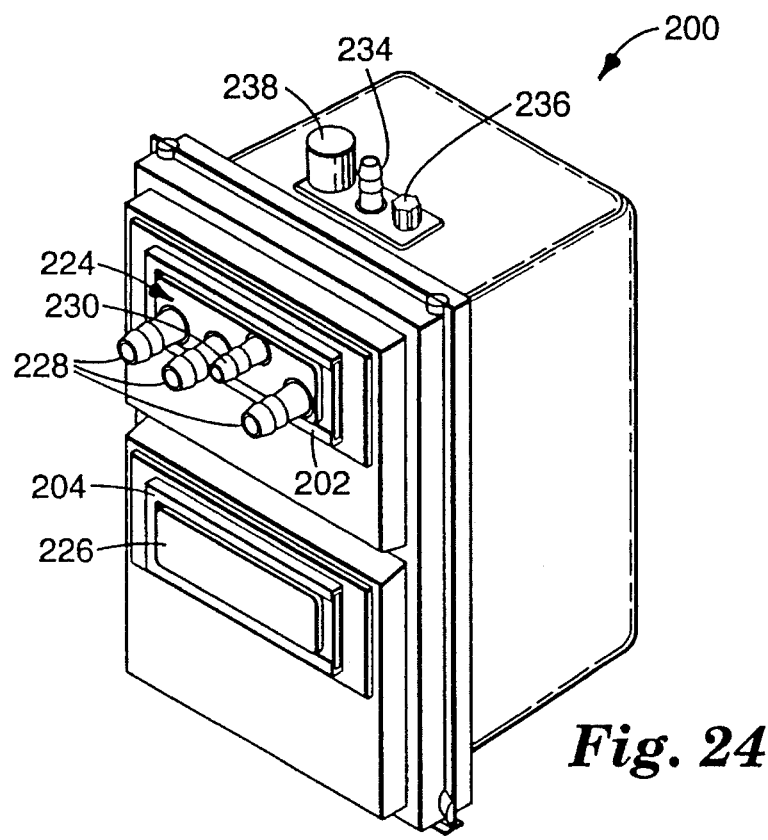
FIGS. 24 and 25 are rear perspective views of the reservoir of FIGS. 19–21, in which a "ICU" connecting block has been positioned in the upper tracks and a sealing block has been positioned in the lower tracks to adapt the reservoir for use after surgery.
Figure 25:
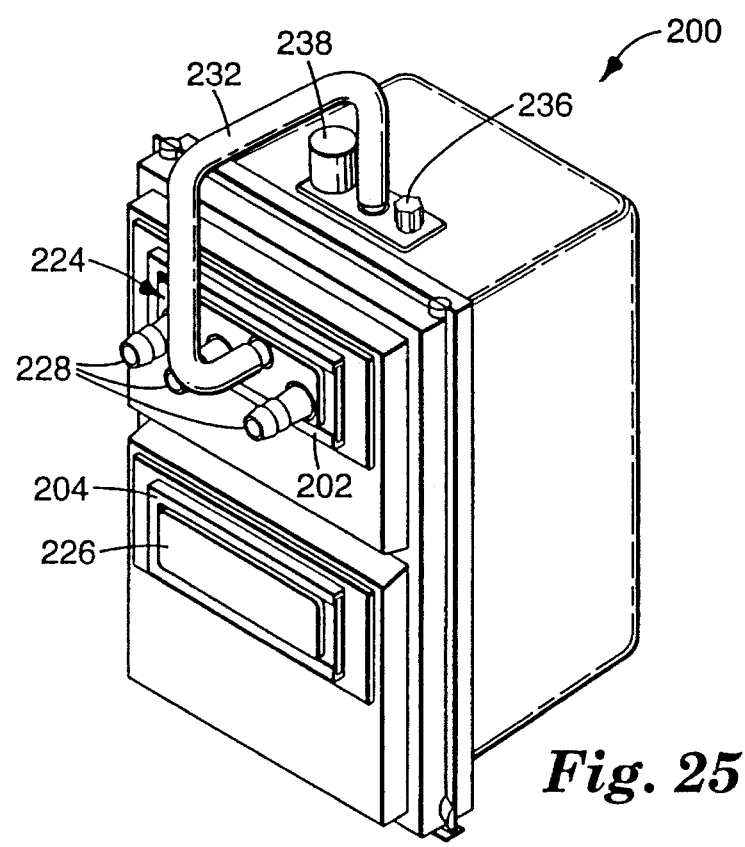

FIGS. 24 and 25 show the reservoir 200 converted for use after surgery for use in collecting blood drained from the chest cavity. This conversion is performed simply by removing blocks 206 and 208 from tracks 202 and 204, and inserting drainage connector block 224 and closed block 226. The closed block 226 does not have any connection posts or features because it is intended merely to seal the venous inlets and other inlets into the lower portion of the blood filtering and defoaming chamber (similar to chamber 108). One or more O-rings (not shown) may optionally be provided on the closed block 226 for sealing the venous inlets and other lower inlets/ports.

The drainage connector block 224 includes a plurality, preferably three, of connection posts 228 for connecting a plurality of chest drainage lines to the cardiotomy inlets 212, and a connection post 230 for connecting an overflow line 232 to an overflow connection post 234 on the top of the blood storage chamber (similar to chamber 106). The overflow line 232 allows viewing blood drawn into the overflow line if/when the filtering medium becomes clogged, and for equalizing vacuum between the defoaming and filtering chamber and the blood storage chamber. Also provided are a luer type port 236 (similar to port 130 in FIG. 5) for a vacuum line (not shown), and a pressure/vacuum control valve 238 (similar to valve 134 in FIG. 5).

The connector blocks 206, 208 and 224 allow the various tubing lines to be pre-packaged connected to the connector blocks 206, 208 and 224 to allow these connections to be made simply be fully inserting the appropriate connector blocks 206, 208 and/or 224 in the tracks 202 and 204.

Figure 26:
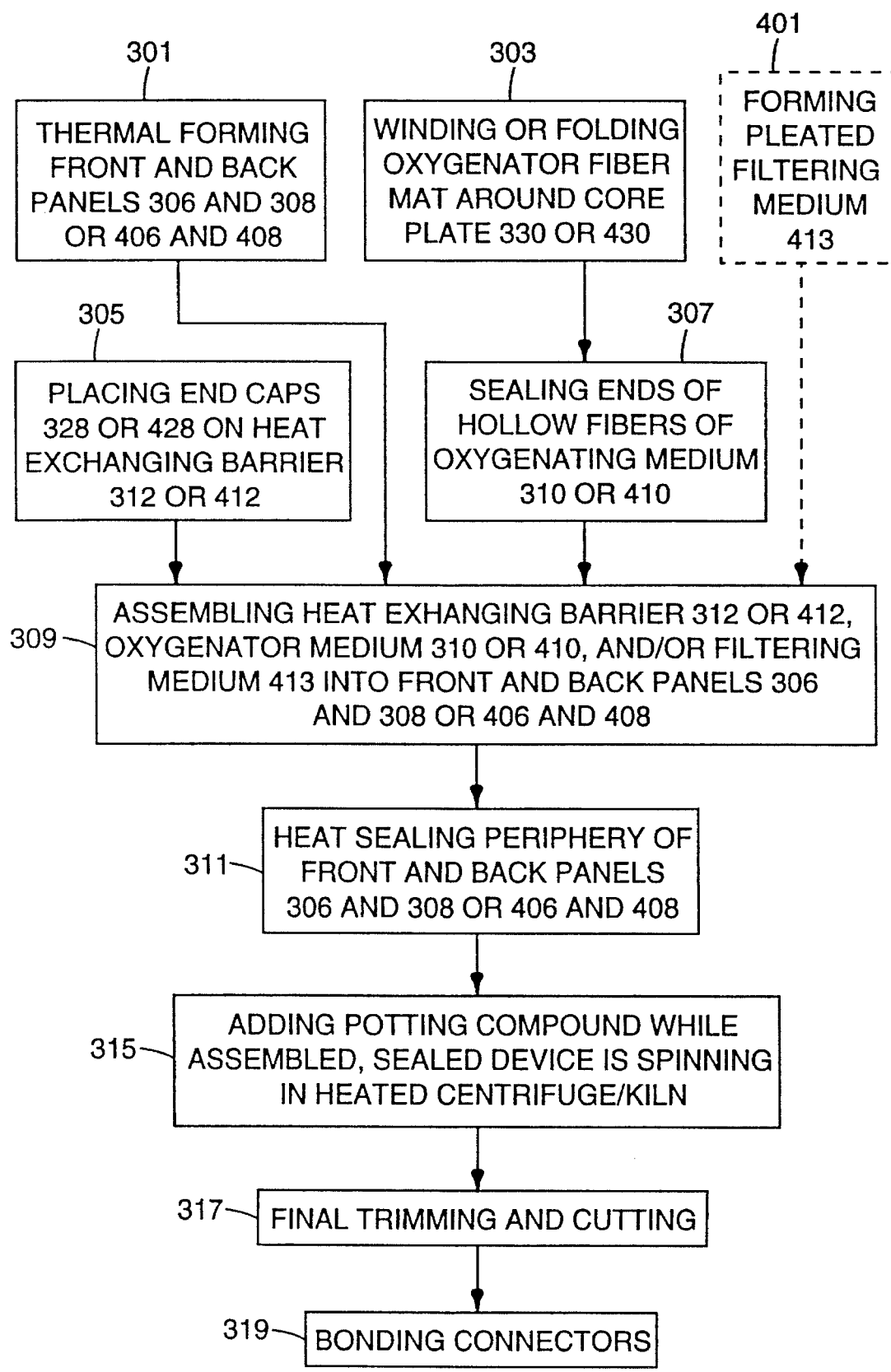
FIG. 26 is a flow chart illustrating the process of making the oxygenating and heat exchanging apparatus of FIG. 3.

FIGS. 26–38 illustrate various aspects of two different embodiments of the oxygenating and heat exchanging device of the invention, designated 300 in FIGS. 26–31 and 400 in FIGS. 33–40, including a novel process for manufacturing the oxygenating and heat exchanging devices 300 and 400 illustrated in part in the flow chart of FIG. 26.

Similar features in FIGS. 26–32 and in FIGS. 32–38 are designed by reference numerals having the same last two digits, with the first digit in the embodiment of FIGS. 26–31 always being "3", and the first digit in the embodiment of FIGS. 32–38 always being "4".

The oxygenating and heat exchanging device 300 is similar to oxygenating and heat exchanging devices 40 and 52 of FIGS. 3 and 4, as well as the device shown at 24 and 26 of FIG. 2. The device 300 includes an oxygenating portion 302 and a heat exchanging portion 304 but does not include an arterial blood filtering section. The device 400 of FIGS. 32–38 shows, in addition to an oxygenating portion 402 and heat exchanging portion 404, an arterial blood filtering section 405.

Figure 29:
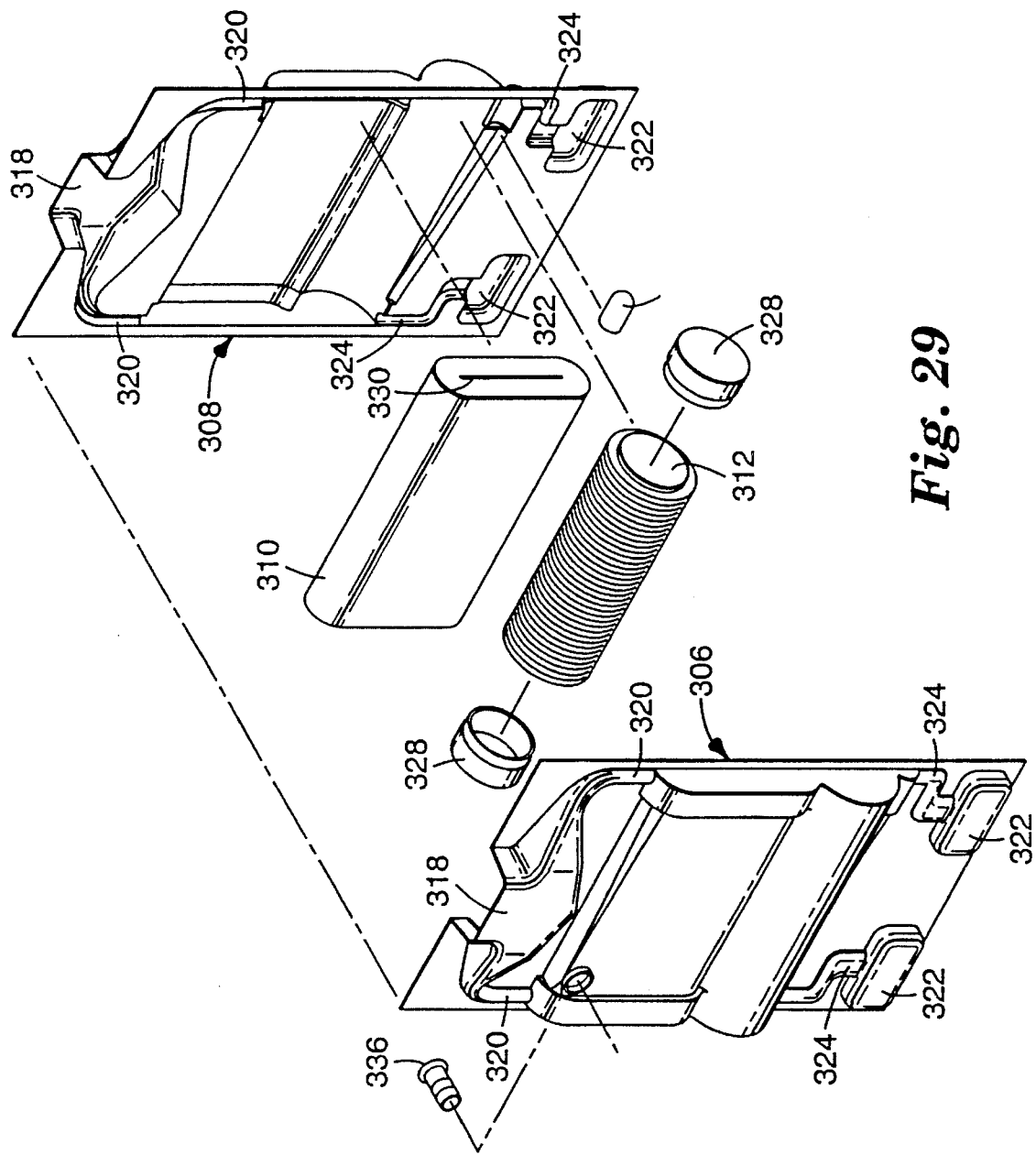
FIG. 29 is a perspective/exploded view of the components, including housing portions cut from the molded sheet of FIG. 28, which are assembled in make the oxygenating and heat exchanging apparatus of FIG. 3.
Figure 34:
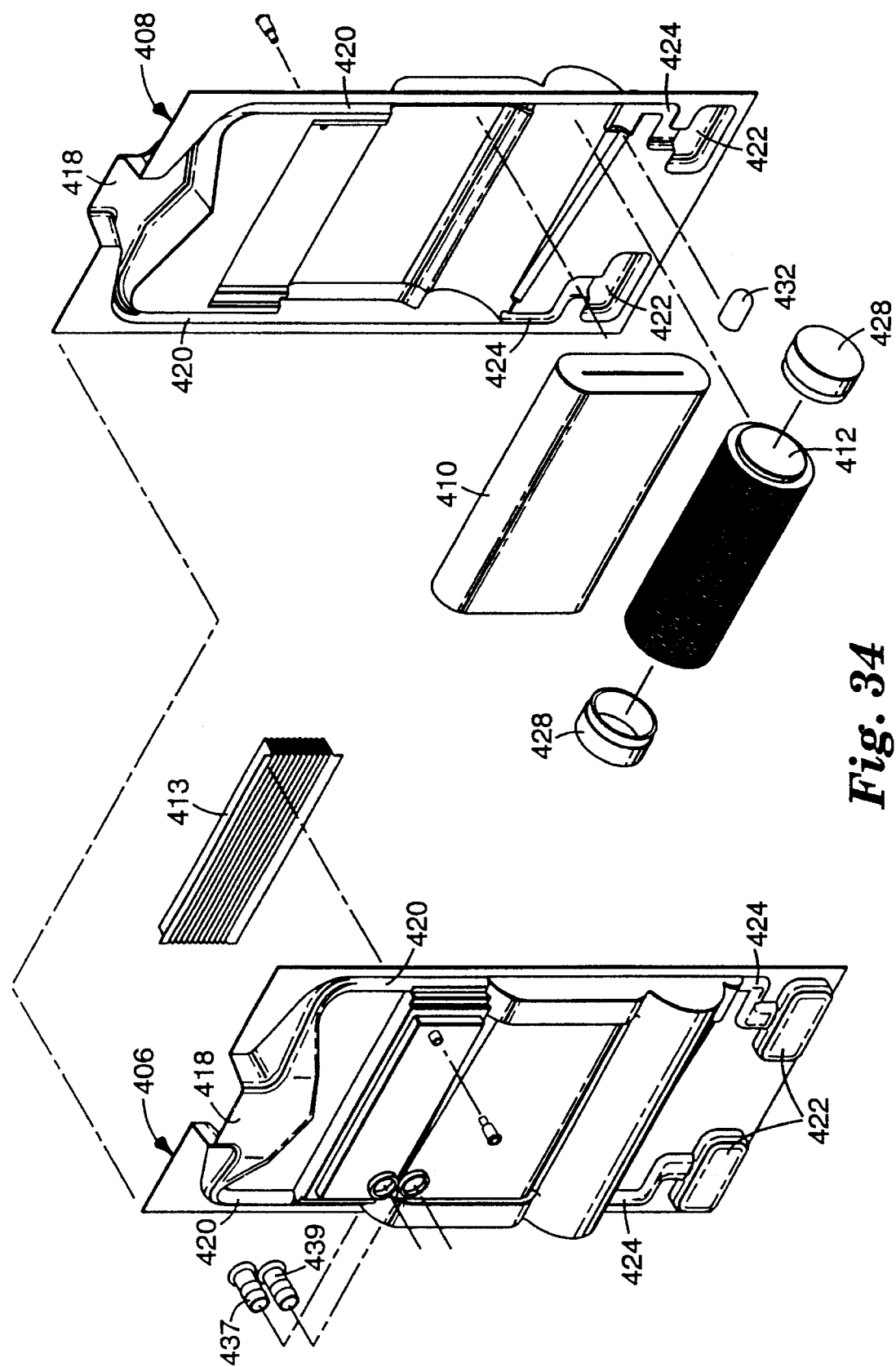
FIG. 34 is a perspective/exploded view of the components, including housing portions cut from the molded sheet of FIG. 33, which are assembled in make an oxygenating and heat exchanging apparatus having an integral arterial blood filter.
Figure 35:
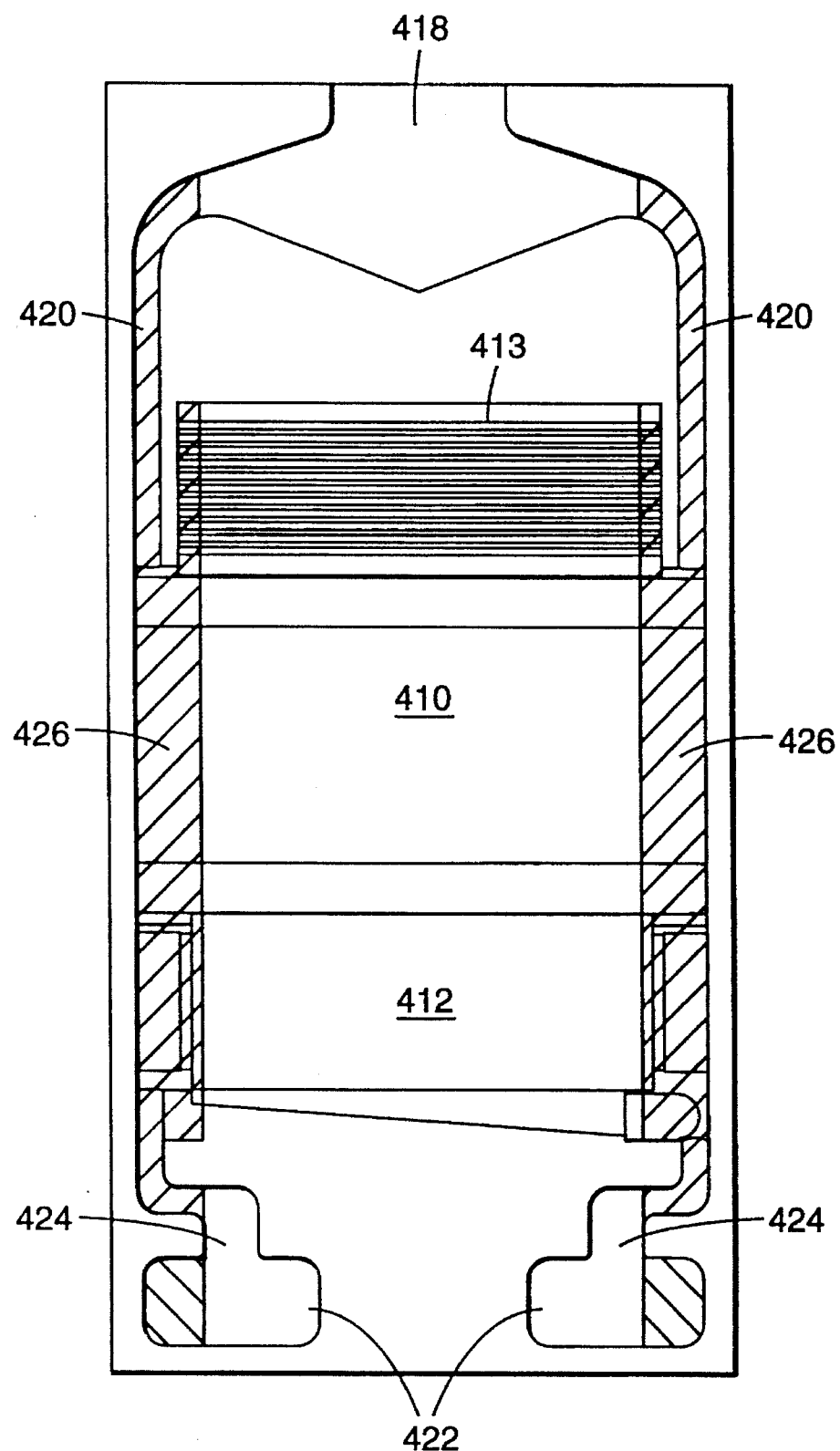
FIG. 35 is a plan view of the assembled components of FIG. 34, illustrating the process of potting adjacent the opposite ends of the components, which is a step in making the oxygenating and heat exchanging apparatus having integral arterial blood filter.

Before discussing the method of manufacturing in detail, the various components shown in the exploded views of FIGS. 29 and 34 will be briefly described. FIGS. 29 and 34 show a front panel 306 or 406 and a back panel 308 or 408. Assembled between the front and back panels 306 or 406 and 308 or 408 are a hollow fiber type blood oxygenating medium 310 or 410, which may be of conventional design such as generally described in U.S. Pat. No. 4,940,617 (incorporated herein by reference); and an undulating, tubular metal heat exchanging barrier 312 or 412, which may be of the type described in U.S. Pat. Nos. 4,846,177 and 5,255,734 (incorporated herein by reference). FIG. 34 also shows a pleated arterial blood filtering medium 413, which is a similar material to the blood filtering medium 122 shown in the reservoir 100 of FIG. 7.

Step 401 in FIG. 26 is pleating the filtering medium 413. Step 309 is assembling the various components, e.g., heat exchanging barrier 312 or 412, oxygenating medium 310 or 412, filtering medium vinyl cap 332 or 432, and/or filtering medium 413 between the front and back panels 306 and 308 or 406 and 408.

Figure 27:
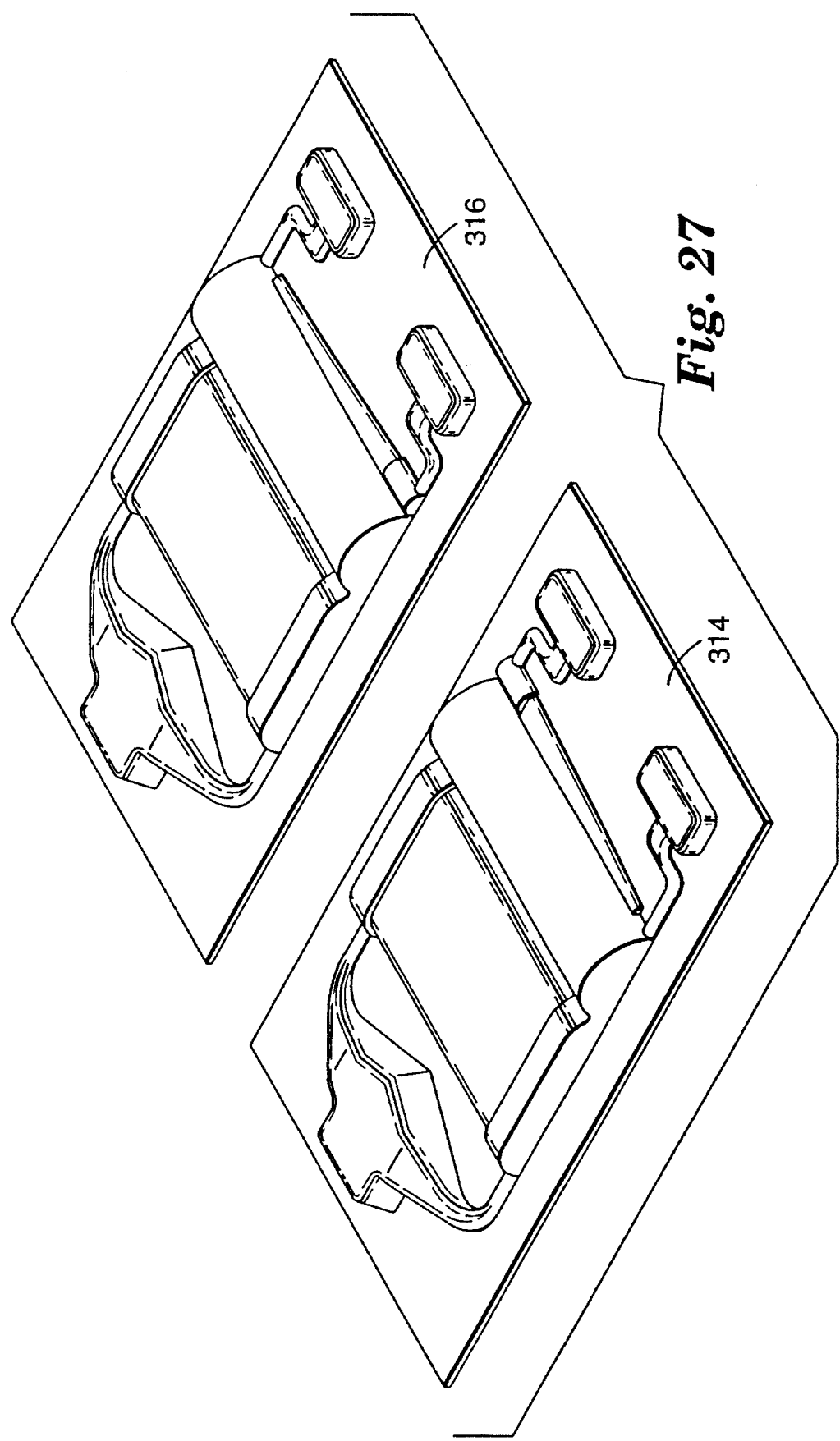
FIG. 27 is a perspective view of a vacuum mold base for the oxygenating and heat exchanging apparatus of FIG. 3.
Figure 28:
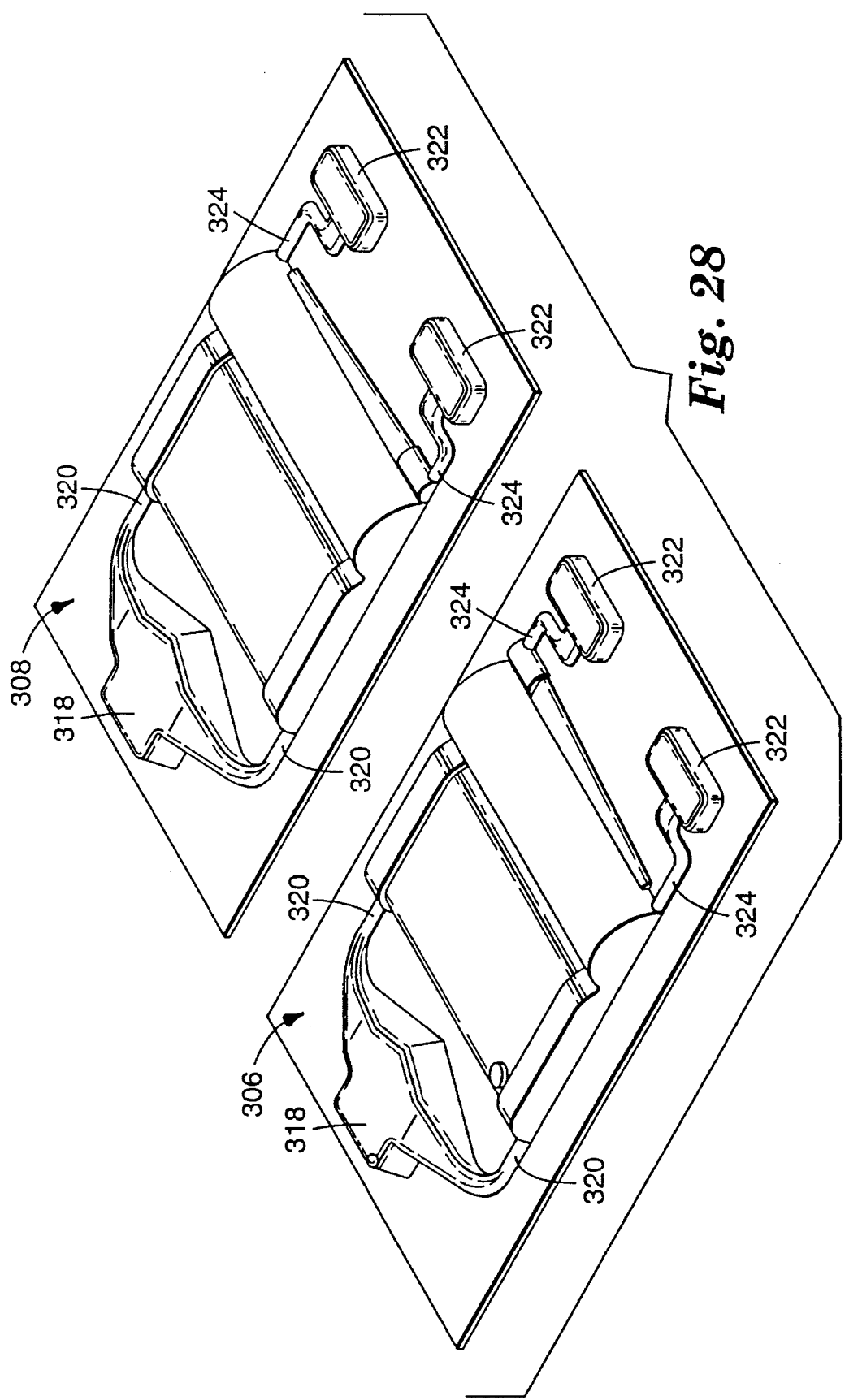
FIG. 28 is a perspective view of an uncut, molded sheet formed on the mold base of FIG. 27.
Figure 32:
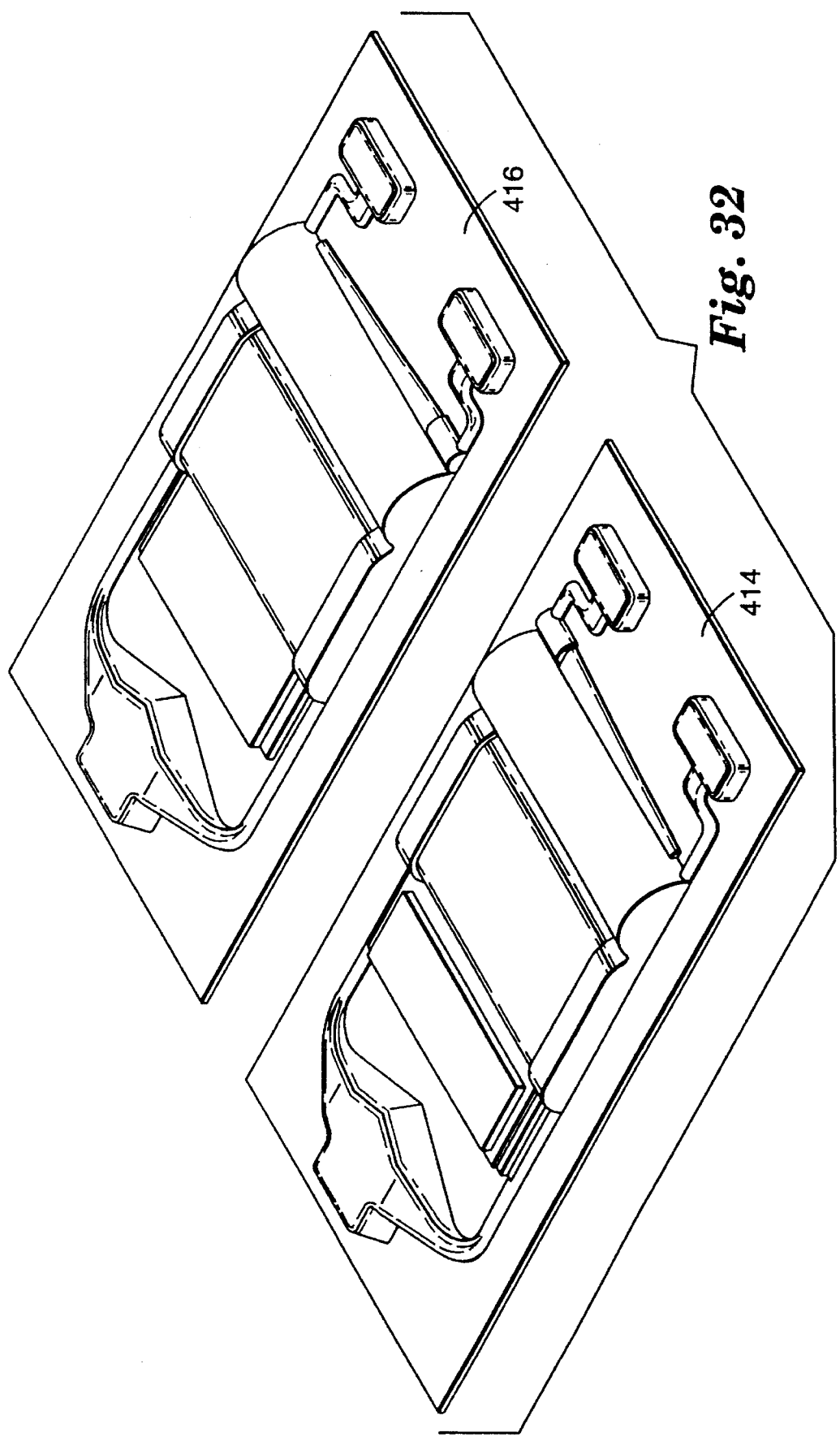
FIG. 32 is a perspective view of a vacuum mold base for use in making an oxygenating and heat exchanging apparatus having an integral arterial blood filter.
Figure 33:
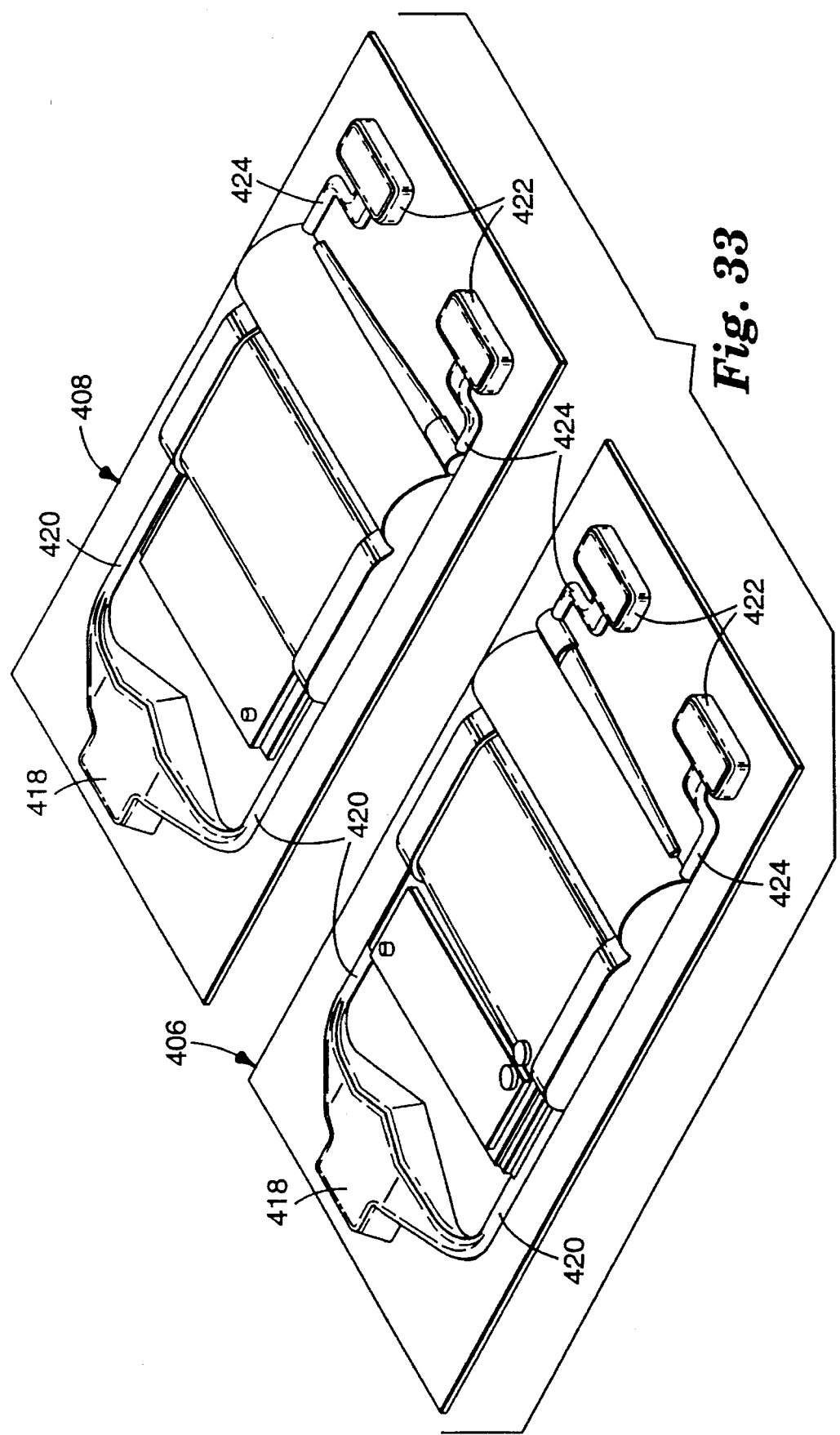
FIG. 33 is a perspective view of an uncut, molded sheet formed on the mold base of FIG. 32.

FIGS. 27 and 32 show aluminum molds 314 or 414 and 316 or 416 for thermal forming the front and back panels 306 and 308 or 406 and 408 (step 301), with the resulting panels shown in FIGS. 28 and 33. As shown in FIGS. 28 and 33, the resulting front and back panels 306 and 308 or 406 and 408 include some features similar to those described above with respect to the blood reservoir 100.

These features include a potting boat 318 or 418 having a generally V-shaped bottom sloping gently upwardly from its center and extending outwardly into opposite downwardly-extending potting channels 320 and 420. The potting boats 318 and 418 are open along their tops to facilitate pouring potting compound (preferably urethane resin) into the boats 318 or 418, with the V-shaped bottom facilitating even distribution of the potting compound into the potting channels 320 or 420. See, e.g., step 315 which follows step 311 of heat sealing the periphery of the front and back panels 306 and 308 or 406 and 408.

Figure 30:
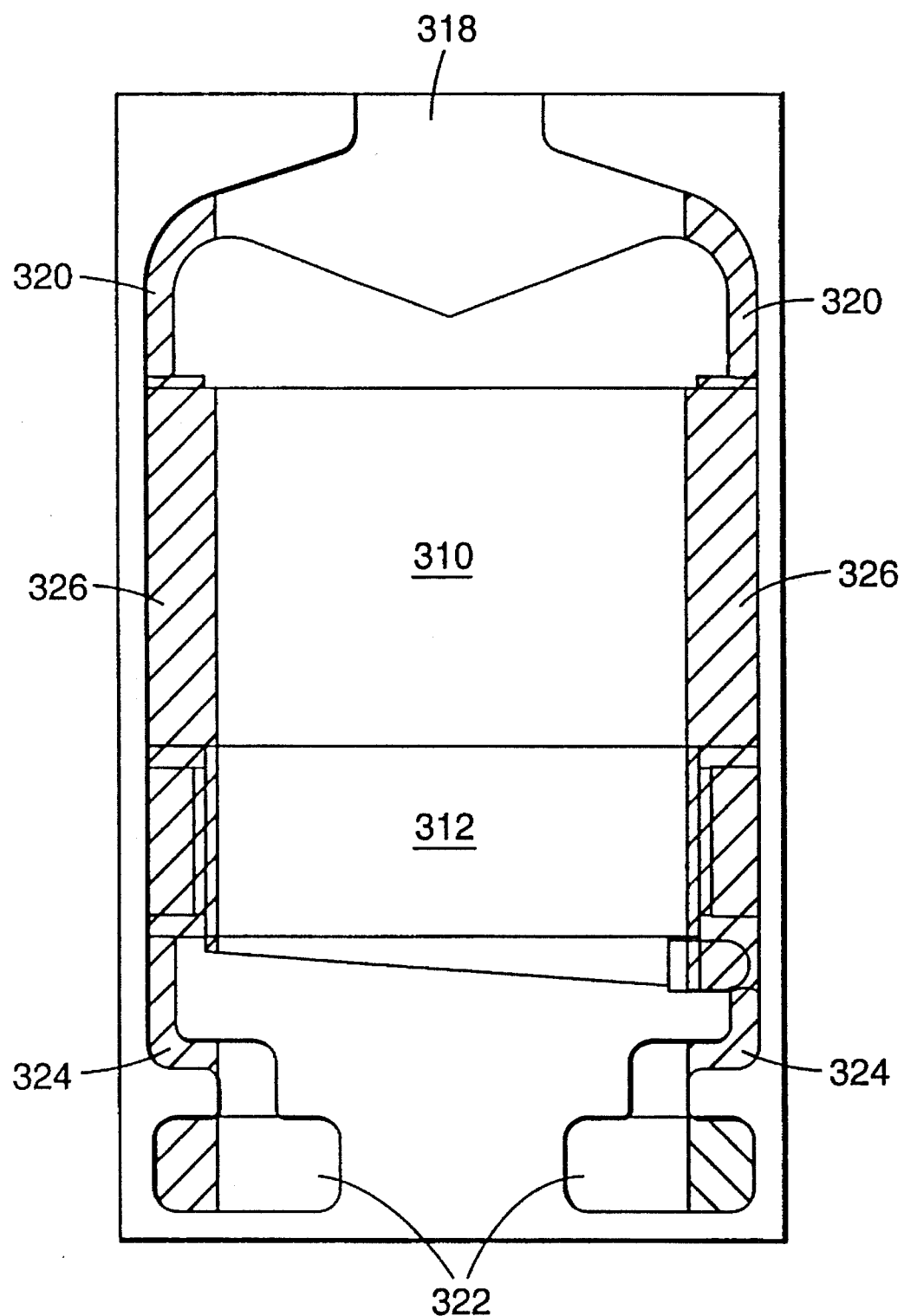
FIG. 30 is a plan view of the assembled components of FIG. 29, illustrating the process of potting adjacent the opposite ends of the components, which is a step in making the oxygenating and heat exchanging apparatus of FIG. 3.
Figure 31:
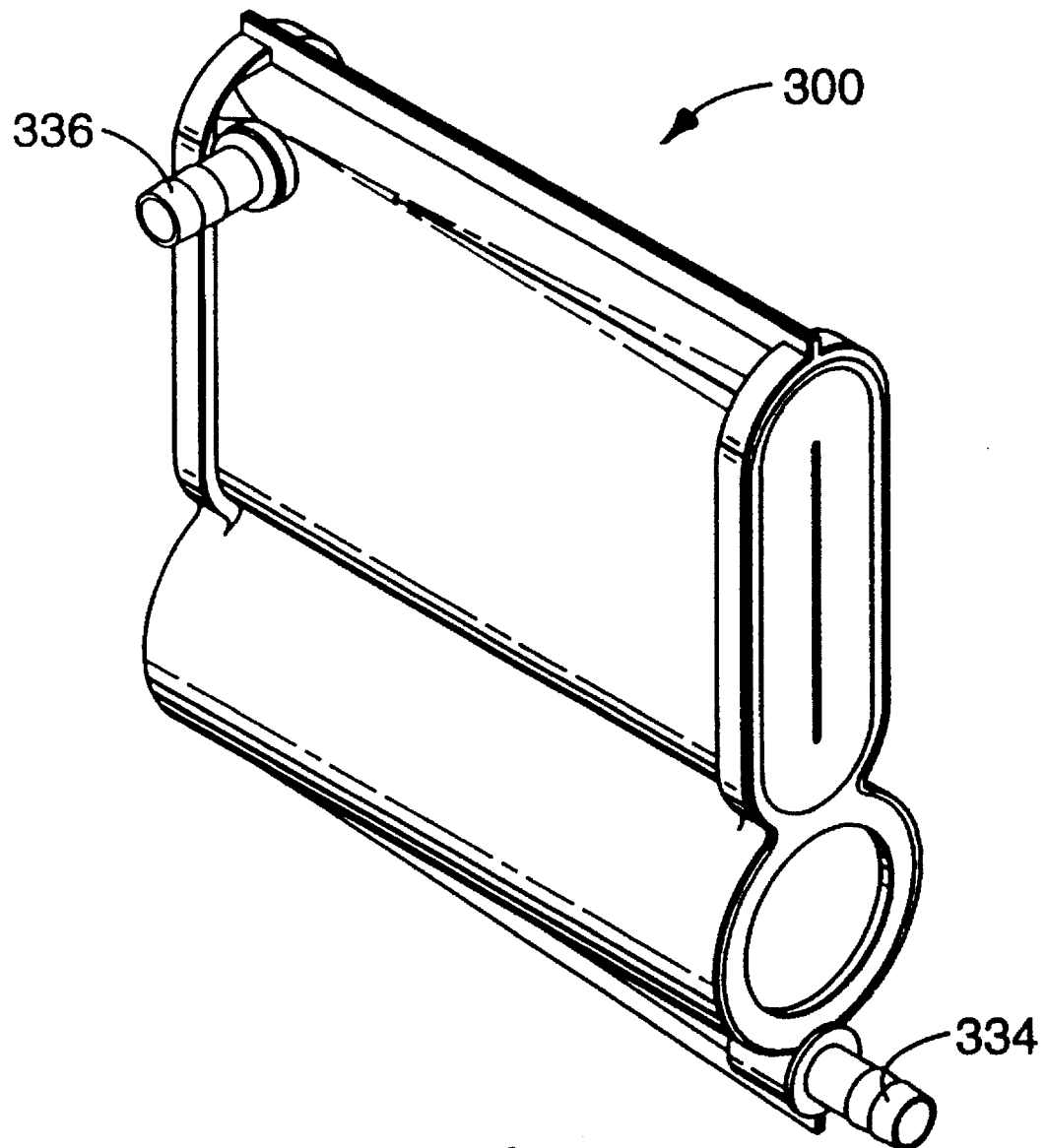
FIG. 31 is a perspective view of an oxygenating and heat exchanging apparatus like that shown in FIG. 3 made according to the process illustrated in FIGS. 26–30.
Figure 36:
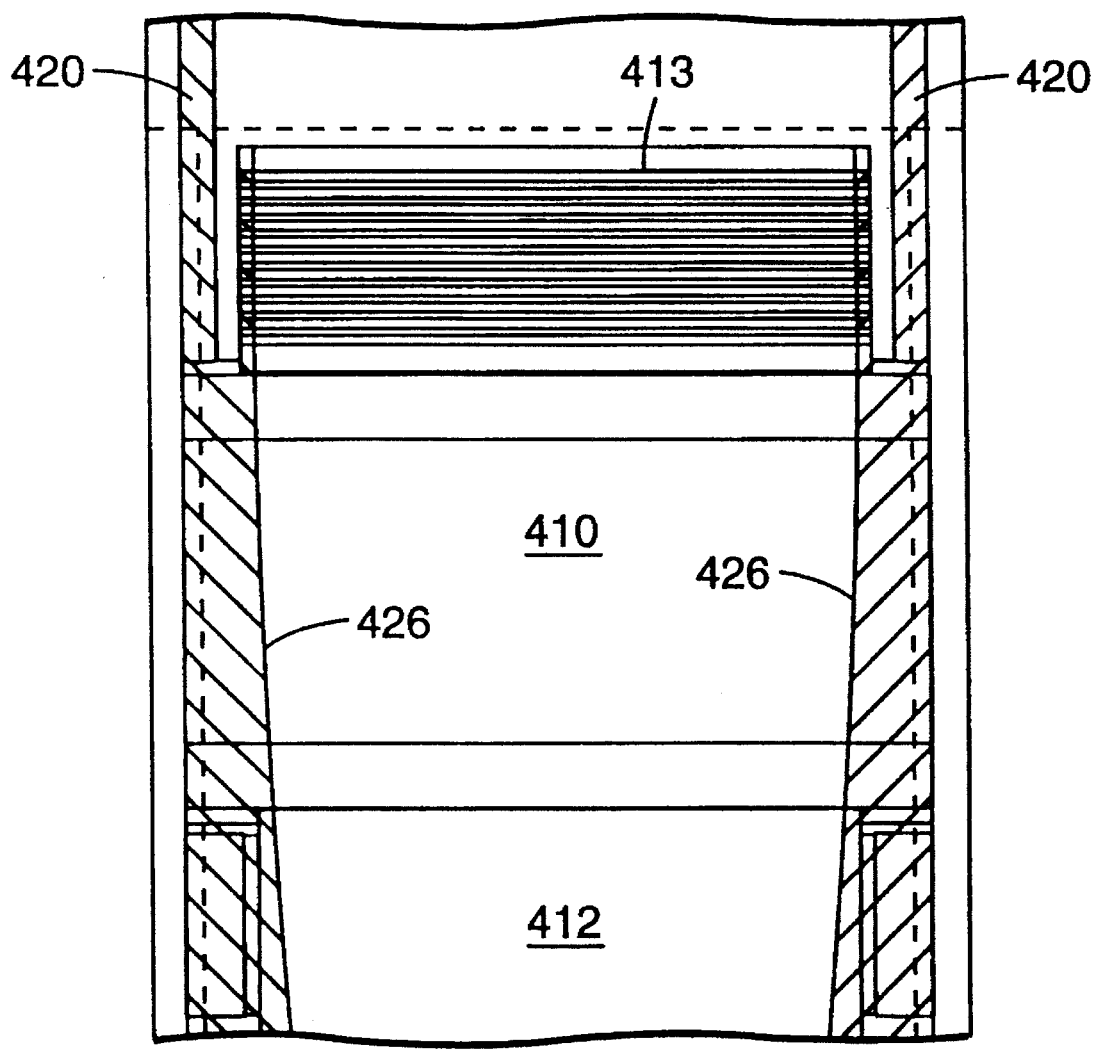
FIG. 36 is a second plan view similar in many respects to FIG. 35 illustrating the arcuate surface of the potting compound formed in the centrifuge/kiln apparatus, and illustrating cut lines where the housing is cut after the potting step is completed.

Also shown in FIGS. 28 and 30 are overflow reservoirs 322 or 422 for receiving excess potting compound. The overflow reservoirs 322 or 422 include inlets 324 or 424 which have a configuration extending generally radially inwardly relative to the axis of rotation of the assembled but unfinished devices 300 or 400 in the centrifuge/kiln (not shown but similar to centrifuge/kiln 188). The arrangement is such that the overflow-reservoir inlets 324 or 424 allow the potting compound reaches a specific depth along the opposite sides of the devices 300 or 400. In this regard, please note the depth of potting compound 326 or 426 illustrated in FIGS. 30, 35 and 36. FIG. 36 illustrates that the actual depth of the potting compound 426 is generally along a parabolic curve (also 426), and the components may be positioned to account for this curve.

FIGS. 29 and 34 show additional features relating to the process for making the devices 300 or 400. Before the components are assembled, polyethylene end caps 328 or 428 are used to plug the opposite ends of the heat exchanging barrier 312 or 412 to prevent entry or potting compound into the internal space of the barrier 312 or 412 (see step 305 of FIG. 26). These caps 328 or 428 are removed or cut off after the potting compound has cured, preferably cut off in one integral operation with a step 317 of cutting the opposite sides of the devices 300 and 400 to expose the water path of the heat exchanger portion and the gas path of the oxygenating portion. The arrangement may be such that only the cap 328 or 428 at one end of the barrier 312 or 412 is cut off or removed, leaving the other end sealed.

The filtering medium 413 of device 400, however, is positioned to avoid cutting the filtering medium 413 when cutting the opposite ends of the oxygenator fibers and the caps 428 in step 317.

In alternate arrangements involving an undulating, generally tubular heat exchanging barrier like 312 or 412 but a different water path mechanism than described in U.S. Pat. Nos. 4,846,177 and 5,255,734, an internal thin-plastic water baffle (not shown) may be provided inside the heat exchanging barrier 312 or 412. Such a baffle is forced into position by water pressure.

The ends of the hollow fibers of the oxygenating medium 310 or 410 are also sealed in step 307 before the step 315 of introducing potting compound into the assembled devices 300 or 400. The hollow fibers may be wound around a core plate 330 or 430 (step 303), with the plate 330 or 430 being internal to the final plane cuts through the potting compound. The final plane cuts expose the internal lumens of the hollow fibers to allow gas passage therethrough. The arrangement is similar with respect to embodiments having a hollow fiber type heat exchanger (not shown).

A vinyl cap 332 or 432 is provided to seal the blood inlet into the heat exchanging portion of the device 300 or 400 to prevent the ingress of potting compound, thereby providing an inlet opening through the potting compound. A tubing connection post 334 or 434 (FIGS. 31 and 37) is then mounted on the inlet opening.

A blood outlet connection post 336 is mounted adjacent the top of the oxygenating portion of device 300, with blood traveling generally upwardly through the housing consecutively through the heat exchanging and blood oxygenating portions of the device 300.

Figure 37:
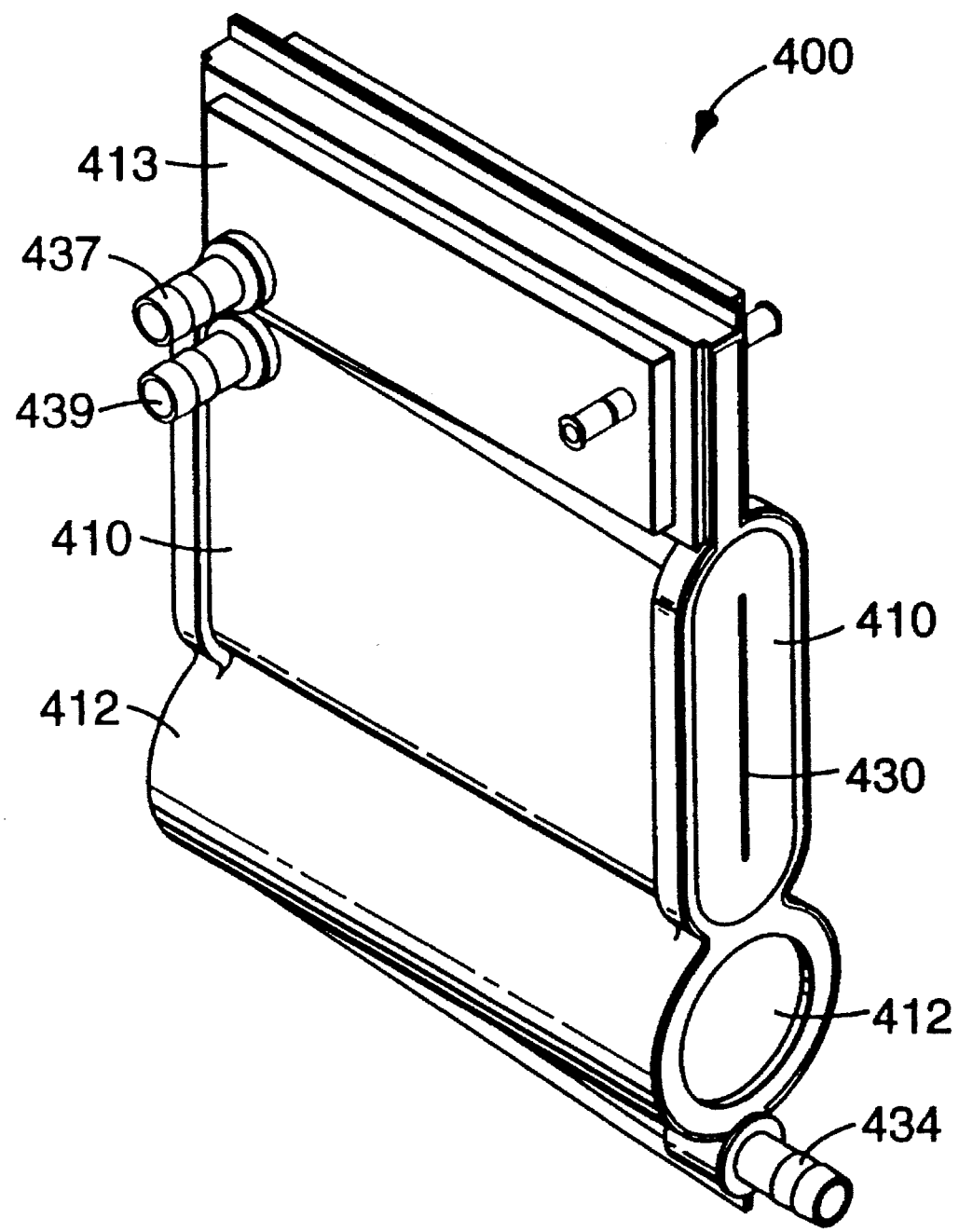
FIG. 37 is a perspective view of the oxygenating and heat exchanging apparatus having integral arterial blood filter, which is made according to the process illustrated in FIGS. 32–36.
Figure 38:
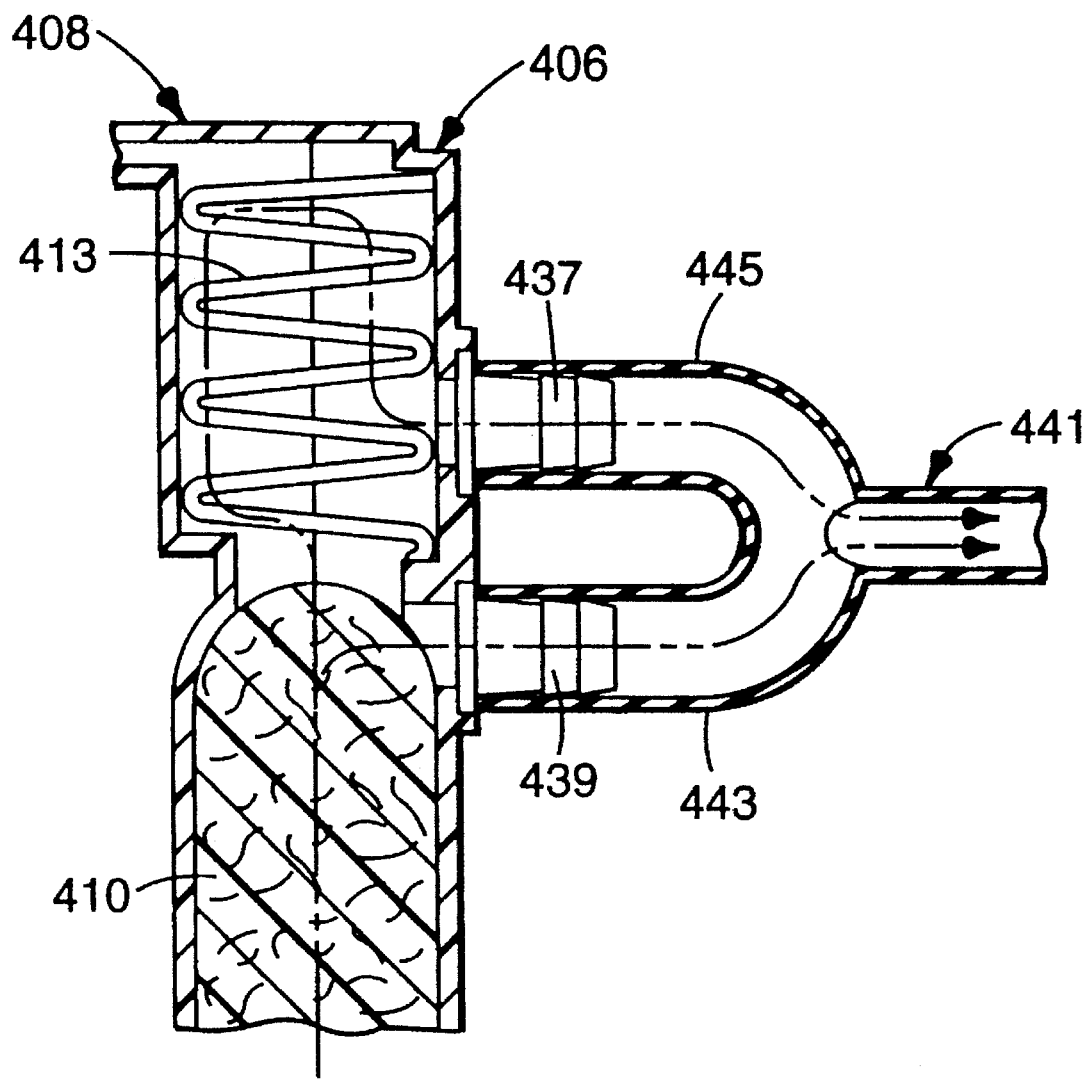
FIG. 38 is a cross sectional view of a portion of the oxygenating and heat exchanging apparatus having integral arterial blood filter, illustrating blood flow through the filter medium and a bypass route for bypassing the filter medium in case it becomes clogged.

In the case of device 400, a blood outlet post 437 is mounted adjacent the top of the filtering portion of the device 400, with blood traveling generally upwardly through the housing consecutively through the heat exchanging, blood oxygenating and blood filtering portions from the inlet connection post 434 to the outlet tubing connection post 437. As illustrated in FIGS. 37 and 38 a filter bypass connection post 439 is mounted adjacent the top of the blood oxygenating portion. A branched outlet tube 441 (FIG. 38) includes a bypass leg 443 connected to post 439 and a normal outlet leg 445 connected to post 437. In normal operation, the bypass leg 443 is clamped off, and blood passes from the filtering portion through the normal outlet leg 443. If the filtering medium 413 becomes clogged, the bypass leg 443 is unclamped to allow blood to bypass the filtering medium 413.

The step 319 is to bond the various connectors described above to the housing of the device 300 or 400.

Figure 39:
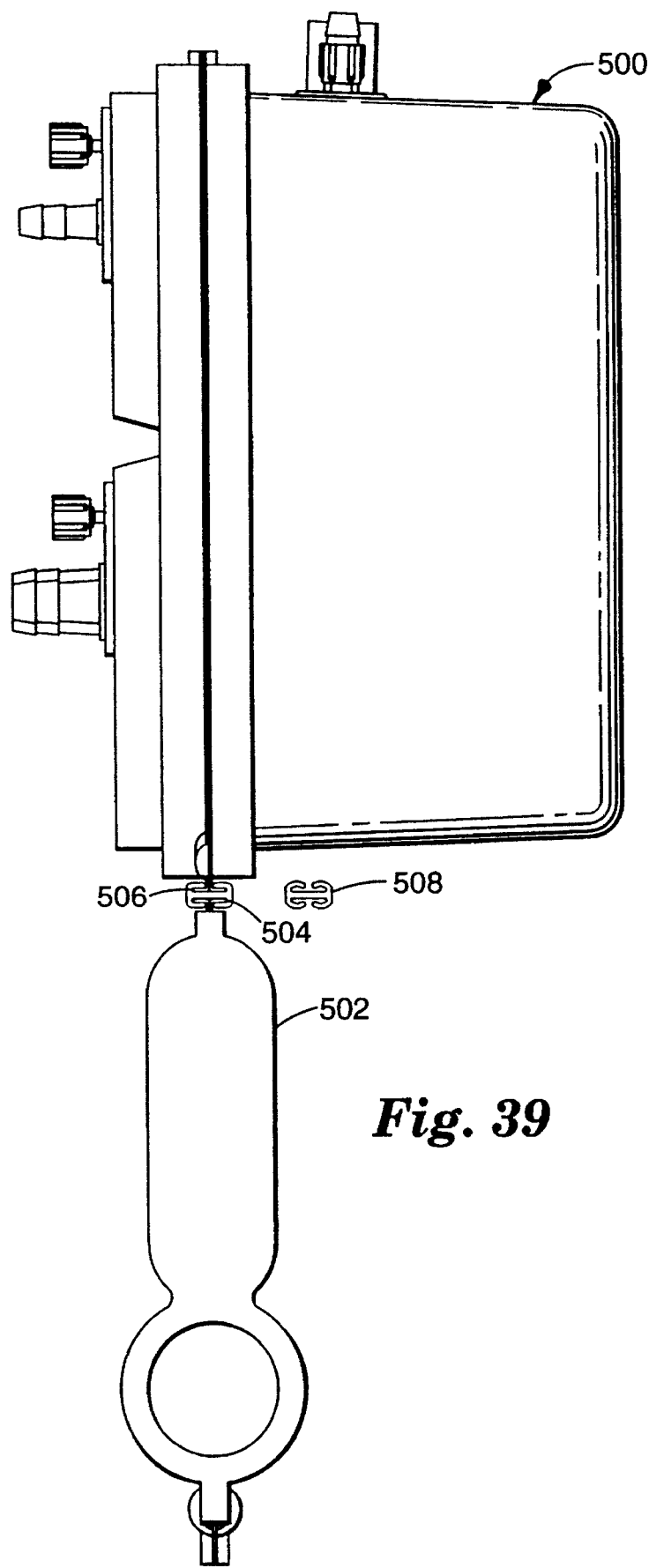
FIG. 39 is a side elevational view of an integral venous/cardiotomy blood reservoir of the invention mounted on an oxygenating and heat exchanging apparatus of the invention.
Figure 40:
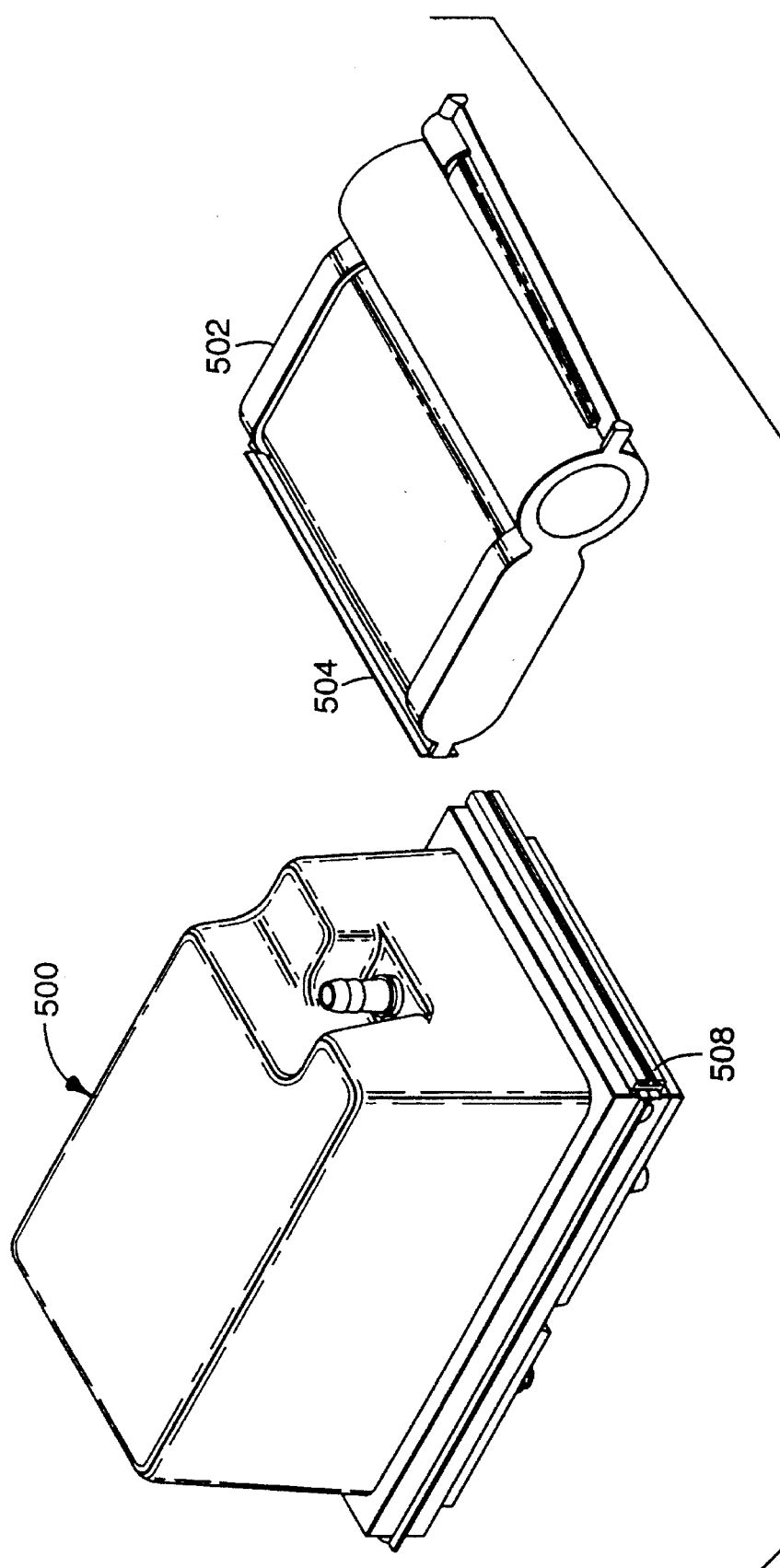
FIG. 40 is a perspective view of the venous/cardiotomy reservoir and oxygenating and heat exchanging apparatus of FIG. 39 illustrating the reservoir and apparatus before the reservoir is mounted on the apparatus.
Figure 41:
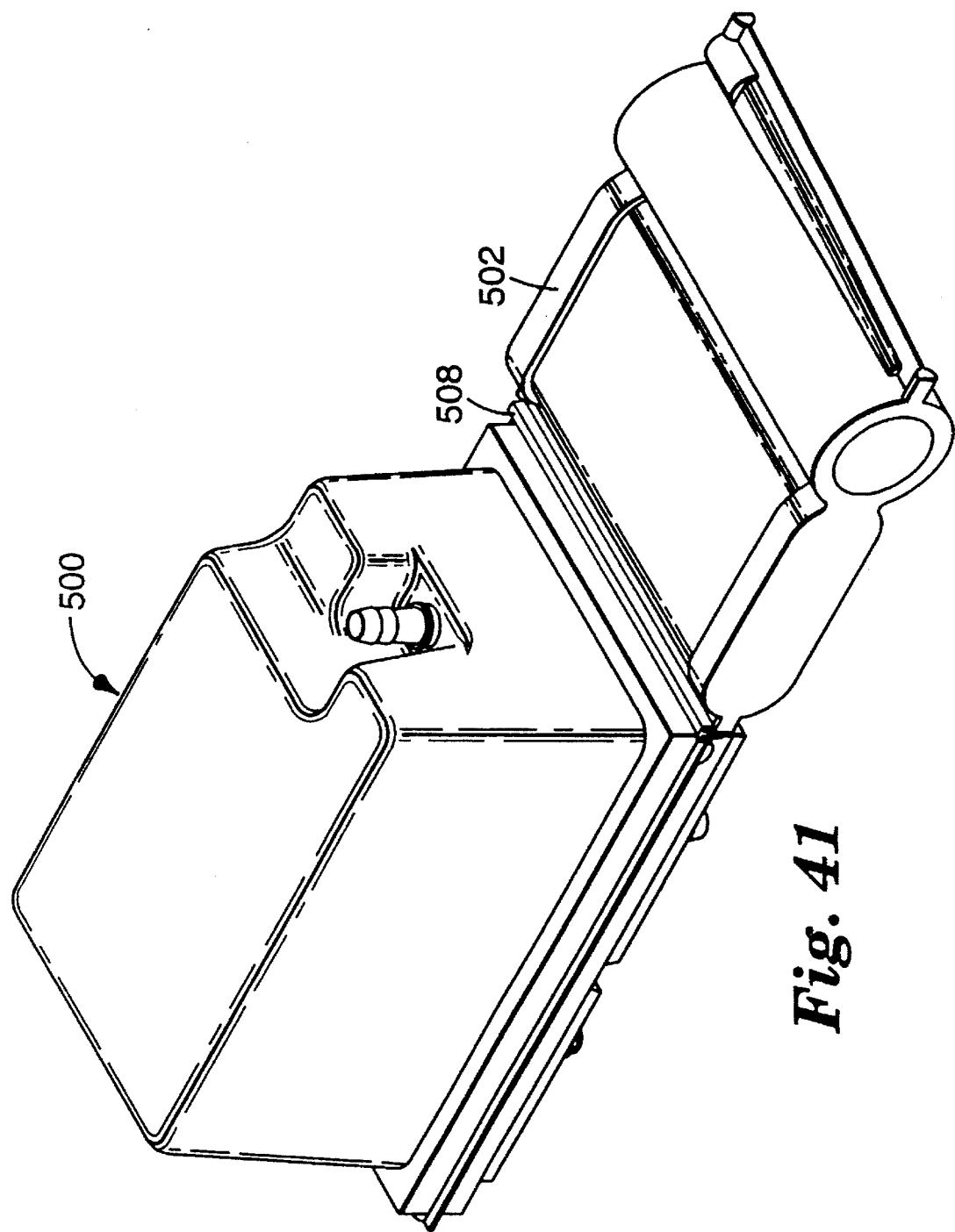
FIG. 41 is a rear elevational view of the venous/cardiotomy reservoir mounted on the oxygenating and heat exchanging apparatus of FIGS. 39–40.

FIGS. 39–41 illustrate various aspects of one way of interconnecting the reservoir, herein designated 500 and the blood oxygenating and heat exchanging device, here designated 502. The top of the blood oxygenating and heat exchanging device 502 may be provide with a generally T-shaped flange 504 and the bottom of the reservoir 500 may be provided with a corresponding inverted, generally T-shaped flange 506. The arrangement is such as to allow an elongate clip 508 to be used to lock the reservoir 500 and blood oxygenating and heat exchanging device 502 together. The clip 508 and T-shaped flanges 504 and 506 are preferably provided with sufficient resilience to provide a resilient locking action.

Other possible arrangements include bonding the reservoir to the oxygenating and heat exchanging device, or providing a thermal-formed packaging-type framework for holding the reservoir and oxygenating and heat exchanging device.

As various changes could be made in the constructions and methods described above without departing from the scope of the invention, it is intended that all matter contained in the description above or shown in the accompanying drawings be interpreted as illustrative and not in a limiting sense.

We claim:

1. An integral blood oxygenating and heat exchanging apparatus for oxygenating blood and heating or cooling blood, the apparatus being adapted to be operatively connected with a mounting device that brings a source of oxygen rich gas and heat-exchanging fluid into fluid communication with the apparatus, the apparatus comprising:

a separation medium comprising hollow fibers for separating blood and gas while permitting transfer of oxygen and carbon dioxide across the medium to oxygenate the blood, the separation medium being arranged in an array having opposite ends, the hollow fibers having internal lumens with open ends open at the opposite ends of the separation medium such that gas may flow through the lumens of the hollow fibers;

a heat exchanging barrier for separating blood and a heat-exchanging fluid while permitting heat transfer across the barrier to heat or cool the blood, the barrier having opposite ends positioned generally adjacent and generally aligned with the opposite ends of the separation medium, the heat exchanging barrier having at least one internal lumen with open ends open at the opposite ends of the heat exchanging barrier;

a housing holding the separation medium and the heat exchanging barrier, the housing being formed into a configuration corresponding to the separation medium and the heat exchanging barrier without enclosing the open ends of the lumens of the hollow fibers of the separation medium and the open ends of the lumen of the heat exchanging barrier; and potting compound sealing the housing adjacent the ends of the separation medium and heat exchanging barrier without closing the open ends of the lumens of the hollow fibers of the separation medium and the open ends of the lumen of the heat exchanging barrier;

a blood inlet and outlet into the housing defining a blood flow path inside the housing across the separation medium outside of the hollow fibers and along the outside of the heat exchanging barrier; and the open ends of the lumens of the hollow fibers and the open ends of the lumen of the heat exchanging barrier opening directly into the environment outside the housing to allow them to be brought into direct fluid communication with the device.

2. Apparatus according to claim 1 wherein the housing includes opposite walls along opposite sides of the separation medium, the blood flow path being defined between the opposite walls of the housing along the outside of the hollow fibers of the separation medium, the opposite walls being resiliently-flexible within a range of flexure to allow the opposite walls to be compressed toward one another to adjust oxygenation of blood flowing through the blood flow path.

3. An apparatus according to claim 1 wherein the housing is formed of thermoplastic material that is vacuum formed to closely receive the separation medium and heat exchanging barrier.

4. A combination of an integral blood oxygenating and heat exchanging apparatus for oxygenating blood and heating or cooling blood with a mounting device that brings a source of oxygen rich gas and heat-exchanging fluid into fluid communication with the apparatus;

the apparatus comprising:

a separation medium comprising hollow fibers for separating blood and gas while permitting transfer of oxygen and carbon dioxide across the medium to oxygenate the blood, the separation medium being arranged in an array having opposite ends, the hollow fibers having internal lumens with open ends open at the opposite ends of the separation medium such that gas may flow through the lumens of the hollow fibers;

a heat exchanging barrier for separating blood and a heat-exchanging fluid while permitting heat transfer across the barrier to heat or cool the blood, the barrier having opposite ends positioned generally adjacent and generally aligned with the opposite ends of the separation medium, the heat exchanging barrier having at least one internal lumen with open ends open at the opposite ends of the heat exchanging barrier;

a housing holding the separation medium and the heat exchanging barrier, the housing being formed into a configuration corresponding to the separation medium and the heat exchanging barrier without enclosing the open ends of the lumens of the hollow fibers of the separation medium and the open ends of the lumen of the heat exchanging barrier; and potting compound sealing the housing adjacent the ends of the separation medium and heat exchanging barrier without closing the open ends of the lumens of the hollow fibers of the separation medium and the open ends of the lumen of the heat exchanging barrier;

a blood inlet and outlet into the housing defining a blood flow path inside the housing across the separation medium outside of the hollow fibers and along the outside of the heat exchanging barrier; and the open ends of the lumens of the hollow fibers and the open ends of the lumen of the heat exchanging barrier opening directly into the environment outside the housing to allow them to be brought into direct fluid communication with the device;

the mounting device comprising:

a mounting bracket for releasably receiving and supporting the apparatus, the mounting bracket being configured to closely receive the apparatus to support the weight of the apparatus;

means in the mounting bracket for engaging the apparatus to form a seal with the apparatus adjacent the open ends of the lumens of the hollow fibers of the separation medium and to bring the lumens of the hollow fibers into fluid communication with a source of oxygen rich gas; and means in the mounting bracket for engaging the apparatus to form a seal with the apparatus adjacent the open ends of the lumen of the heat exchanging barrier and to bring the lumen of the heat exchanging barrier into fluid communication with a source of heat exchanging fluid.

5. A combination according to claim 4 wherein:

the housing of the apparatus includes opposite walls along opposite sides of the separation medium, the blood flow path being defined between the opposite walls of the housing along one surface of the separation medium, the opposite walls being resiliently-flexible within a range of flexure to allow the opposite walls to be compressed toward one another to adjust oxygenation of blood flowing through the blood flow path; and the device further includes means in the mounting bracket for compressing the opposite walls of the housing toward one another to adjust oxygenation of blood flowing through the blood flow path.

6. A combination according to claim 4 wherein the mounting bracket supports the housing of the apparatus against internal pressure in the housing.

7. An extracorporeal circulatory support circuit for supporting a patient during cardiopulmonary bypass, the circuit comprising:

blood reservoir having a defoaming and filtering chamber and a blood storage chamber in fluid communication with the defoaming and filtering chamber, the reservoir having at least one cardiotomy blood inlet and at least one venous blood inlet into the defoaming and filtering chamber and an outlet for draining the blood storage chamber, the defoaming and filtering chamber including defoaming and filtering mediums; and an integral blood oxygenating and heat exchanging apparatus for oxygenating blood and heating or cooling blood, the apparatus being adapted to be operatively connected with a device that brings a source of oxygen rich gas and heat-exchanging fluid into fluid communication with the apparatus, the apparatus comprising:

a separation medium comprising hollow fibers for separating blood and gas while permitting transfer of oxygen and carbon dioxide across the medium to oxygenate the blood, the separation medium being arranged in an array having opposite ends, the hollow fibers having internal lumens with open ends open at the opposite ends of the separation medium such that gas may flow through the lumens of the hollow fibers;

a heat exchanging barrier for separating blood and a heat-exchanging fluid while permitting heat transfer across the barrier to heat or cool the blood, the barrier having opposite ends positioned generally adjacent and generally aligned with the opposite ends of the separation medium, the heat exchanging barrier having at least one internal lumen with open ends open at the opposite ends of the heat exchanging barrier;

a housing holding the separation medium and the heat exchanging barrier, the housing being formed into a configuration corresponding to the separation medium and heat exchanging barrier without enclosing the open ends of the lumens of the hollow fibers of the separation medium and the open ends of the lumen of the heat exchanging barrier;

potting compound sealing the housing adjacent the ends of the separation medium and heat exchanging barrier without closing the open ends of the lumens of the hollow fibers of the separation medium and the open ends of the lumen of the heat exchanging barrier; and a blood inlet and outlet into the portion of the housing holding the separation medium and heat exchanging barrier, the blood inlet and outlet defining a blood flow path inside the housing across the separation medium outside of the hollow fibers and along the outside of the heat exchanging barrier; and the open ends of the lumens of the hollow fibers and the open ends of the lumen of the heat exchanging barrier being open to allow them to be brought into direct fluid communication with the device;

the blood inlet of the apparatus being in fluid communication with the blood outlet of the reservoir.

8. A circuit according to claim 7 further comprising a blood conduit bringing the outlet of the reservoir into fluid communication with the blood inlet of the apparatus, the blood conduit being adapted for pumping the blood through the blood conduit from the reservoir into the housing of the apparatus.

9. A circuit according to claim 8 further comprising a centrifugal blood pump mounted along the blood conduit to pump blood from the reservoir through the apparatus;

the housing of the apparatus being formed of at least one sheet of thermoplastic material thermal formed into a configuration corresponding to the separation medium and heat exchanging barrier without enclosing the open ends of the lumens of the hollow fibers of the separation medium and the open ends of the lumen of the heat exchanging barrier, the sheet of thermoplastic material forming the housing also including a portion holding the centrifugal blood pump.

10. A circuit according to claim 9 wherein the centrifugal blood pump is releasably held on the sheet of thermoplastic material.

11. A circuit according to claim 8 wherein the blood conduit is formed of resiliently flexible tubing which is adapted to be placed in a positive displacement roller pump to pump blood from the reservoir through the housing of the apparatus.

12. A circuit according to claim 7 wherein the housing of the apparatus includes opposite walls along opposite sides of the separation medium, the blood flow path being defined between the opposite walls of the housing along one surface of the separation medium, the opposite walls being resiliently-flexible within a range of flexure to allow the opposite walls to be compressed toward one another to adjust oxygenation of blood flowing through the blood flow path.

13. A circuit according to claim 7 further comprising a device that brings a source of oxygen rich gas and heat-exchanging fluid into fluid communication with the apparatus, the device comprising:

a mounting bracket for releasably receiving and supporting the apparatus, the mounting bracket being configured to closely receive the housing of the apparatus to support the weight of the apparatus and support the housing of the apparatus against internal pressure in the housing;

means in the mounting bracket for engaging the apparatus to form a seal with the apparatus adjacent the open ends of the lumens of the hollow fibers of the separation medium and to bring the lumens of the hollow fibers into fluid communication with a source of oxygen rich gas; and means in the mounting bracket for engaging the apparatus to form a seal with the apparatus adjacent the open ends of the lumen of the heat exchanging barrier and to bring the lumen of the heat exchanging barrier into fluid communication with a source of heat exchanging fluid.

14. A circuit according to claim 13 wherein:

the housing of the apparatus includes opposite walls along opposite sides of the separation medium, the blood flow path being defined between the opposite walls of the housing along one surface of the separation medium, the opposite walls being resiliently-flexible within a range of flexure to allow the opposite walls to be compressed toward one another to adjust oxygenation of blood flowing through the blood flow path; and the device further includes means in the mounting bracket for compressing the opposite walls of the housing of the apparatus toward one another to adjust oxygenation of blood flowing through the blood flow path.

15. A circuit according to claim 7 wherein the housing of the apparatus is formed of thermoplastic material that is vacuum formed to closely receive the separation medium and heat exchanging barrier.

16. A circuit according to claim 7 wherein the reservoir is mounted on the apparatus above the apparatus.

17. A circuit according to claim 16 further comprising an elongate clip mounting the reservoir on the apparatus.

18. A circuit according to claim 7 wherein the reservoir further comprises:

a housing having walls defining two interior chambers including the blood storage chamber and the defoaming and filtering chamber, each chamber having a top and a bottom, the blood storage chamber and defoaming and filtering chamber being separated from one another by a generally vertical dividing wall formed of substantially liquid impervious material, the dividing wall having a vent generally adjacent the top of the defoaming and filtering chamber communicating with the blood storage chamber, and a port generally adjacent the bottom of the defoaming and filtering chamber communicating with the blood storage chamber;

the blood defoaming and filtering mediums of the reservoir comprising:

a blood filtering medium in the defoaming and filtering chamber for filtering blood to remove clots and other undesired matter from the blood, the blood filtering medium being positioned in the defoaming and filtering chamber such that blood entering the defoaming and filtering chamber from the cardiotomy blood inlet must pass through the blood filtering medium; and a blood defoaming medium taking up substantially the entire space of the defoaming and filtering chamber not occupied by the filtering medium such that blood entering the defoaming and filtering chamber through the cardiotomy blood inlet and venous blood inlet must pass through the blood defoaming medium before exiting the defoaming and filtering chamber through the port.

19. A circuit according to claim 18 wherein the reservoir is mounted on the apparatus above the apparatus.

20. A circuit according to claim 18 wherein the blood filtering medium of the reservoir is positioned such that blood entering the defoaming and filtering chamber through the venous inlet does not pass through the blood filtering medium.

21. A circuit according to claim 20 wherein the reservoir includes a generally vertically extending exterior wall forming, together with the dividing wall, the defoaming and filtering chamber, the cardiotomy blood inlet or inlets being positioned on the exterior wall generally adjacent the top of the defoaming and filtering chamber, and the venous blood inlet or inlets being positioned on the exterior wall generally adjacent the bottom of the defoaming and filtering chamber.

22. A circuit according to claim 21 wherein the walls of the reservoir are formed by thermal forming of thermoplastic material and sealing the walls together along peripheral portions thereof to form the chambers.

* * * * *

UNITED STATES PATENT AND TRADEMARK OFFICE
CERTIFICATE OF CORRECTION

PATENT NO. : 5,514,335
DATED : May 7, 1996
INVENTOR(S) : Ronald J. Leonard, Erin J. Lindsay, David B. Maurer and Daniel W. Viitala It is certified that error appears in the above-indentified patent and that said Letters Patent is hereby corrected as shown below:

Col. 13, line 60, "33-40" should read --32-38--.
Col. 13, line 63, "26-32" should read --26-31--.

Signed and Sealed this

Third Day of March, 1998

Attest:

Attesting Officer

BRUCE LEHMAN

Commissioner of Patents and Trademarks